US009502754B2

United States Patent
Zhao et al.

(10) Patent No.: US 9,502,754 B2
(45) Date of Patent: Nov. 22, 2016

(54) IMPLANTABLE MEDICAL DEVICES HAVING COFIRE CERAMIC MODULES AND METHODS OF FABRICATING THE SAME

(71) Applicant: Medtronic, Inc., Minneapolis, MN (US)

(72) Inventors: Yanzhu Zhao, Blaine, MN (US); Nicholas C. Wine, Minneapolis, MN (US); Joyce K. Yamamoto, Maple Grove, MN (US); Gerardo Aguirre, San Diego, CA (US); Arne Kolbjorn Knudsen, San Diego, CA (US)

(73) Assignee: Medtronic, Inc., Minneapolis, MN (US)

( * ) Notice: Subject to any disclaimer, the term of this patent is extended or adjusted under 35 U.S.C. 154(b) by 261 days.

(21) Appl. No.: 14/163,483

(22) Filed: Jan. 24, 2014

(65) Prior Publication Data

US 2015/0214604 A1  Jul. 30, 2015

(51) Int. Cl.
| | |
|---|---|
| *H01Q 1/12* | (2006.01) |
| *H01Q 1/27* | (2006.01) |
| *A61B 5/00* | (2006.01) |
| *A61N 1/36* | (2006.01) |
| *H01Q 1/24* | (2006.01) |

(Continued)

(52) U.S. Cl.
CPC ............ *H01Q 1/273* (2013.01); *A61B 5/00* (2013.01); *A61N 1/36* (2013.01); *A61N 1/37229* (2013.01); *H01Q 1/24* (2013.01); *H01Q 1/36* (2013.01); *H01Q 7/00* (2013.01); *A61B 2562/12* (2013.01); *Y10T 29/49117* (2015.01)

(58) Field of Classification Search
CPC ............ H01Q 1/27; H01Q 7/00; H01Q 1/24
USPC ................. 343/718, 700 MS, 841; 361/139; 257/659
See application file for complete search history.

(56) References Cited

U.S. PATENT DOCUMENTS

| 6,693,604 B2 | 2/2004 | Washiro et al. |
| 6,708,065 B2 | 3/2004 | Von Arx et al. |

(Continued)

FOREIGN PATENT DOCUMENTS

| CN | 101510530 | 8/2009 |
| EP | 1890765 | 2/2008 |

(Continued)

OTHER PUBLICATIONS (PCT/US2015/012154) PCT Notification of Transmittal of the International Search Report and the Written Opinion of the International Searching Authority, Mailed Mar. 31, 2015, 11 pages.

*Primary Examiner* — Huedung Mancuso

(57) ABSTRACT

An implantable medical device (IMD) and methods of fabricating the same are provided. An IMD can include a housing and a cofire ceramic module (CCM) coupled to the housing. The CCM can include an antenna cofire-integrated in the CCM. The antenna can include a plate composed of conductive material, and conductive antenna elements that are annular substrates having perimeters substantially coextensive with the perimeter of the plate. The antenna can also include interconnections. A first set of interconnections can be coupled between the plate and one of the conductive antenna elements, and a second set of interconnections can be coupled between the conductive antenna elements. The antenna can also include a feed line conductively coupled to the plate. In some embodiments, the feed line can be substantially serpentine-shaped to adjust impedance in the CCM.

23 Claims, 21 Drawing Sheets

(51) Int. Cl.
*H01Q 7/00* (2006.01)
*A61N 1/372* (2006.01)
*H01Q 1/36* (2006.01)

(56) References Cited

U.S. PATENT DOCUMENTS

| | | | |
|---|---|---|---|
| 6,788,254 B2 | 9/2004 | Oh et al. | |
| 6,963,309 B2 | 11/2005 | Anderson et al. | |
| 7,047,076 B1 | 5/2006 | Li et al. | |
| 7,307,597 B2 | 12/2007 | Okayama | |
| 7,317,946 B2 | 1/2008 | Twetan et al. | |
| 7,554,493 B1 | 6/2009 | Rahman | |
| 8,497,804 B2 * | 7/2013 | Haubrich | A61N 1/37229 343/700 MS |
| 8,620,449 B2 | 12/2013 | Zhao et al. | |
| 8,983,618 B2 * | 3/2015 | Yamamoto | A61N 1/37223 607/30 |
| 9,259,582 B2 * | 2/2016 | Joshi | A61N 1/37229 |
| 2006/0092079 A1 * | 5/2006 | de Rochemont | H01Q 1/362 343/700 MS |
| 2007/0060969 A1 | 3/2007 | Burdon et al. | |
| 2007/0060970 A1 | 3/2007 | Burdon et al. | |
| 2007/0100385 A1 | 5/2007 | Rawat et al. | |
| 2007/0236861 A1 * | 10/2007 | Burdon | A61N 1/3754 361/302 |
| 2009/0228074 A1 | 9/2009 | Edgell et al. | |
| 2009/0228076 A1 | 9/2009 | Ameri | |
| 2010/0109958 A1 | 5/2010 | Haubrich et al. | |
| 2010/0109966 A1 | 5/2010 | Mateychuk et al. | |
| 2010/0114246 A1 | 5/2010 | Yamamoto et al. | |
| 2010/0219513 A1 | 9/2010 | Zhang et al. | |
| 2011/0029036 A1 | 2/2011 | Yamamoto et al. | |
| 2012/0001812 A1 | 1/2012 | Zhao et al. | |
| 2013/0208390 A1 | 8/2013 | Singh et al. | |

FOREIGN PATENT DOCUMENTS

| | | |
|---|---|---|
| EP | 1924321 | 5/2008 |
| EP | 2367597 | 9/2011 |
| EP | 2389711 | 11/2011 |
| TW | 200421669 | 10/2004 |
| TW | 292170 | 6/2006 |
| WO | 2008032746 A1 | 3/2008 |
| WO | 2010078100 | 7/2010 |
| WO | 2011037648 | 3/2011 |

* cited by examiner

IMPLANTABLE MEDICAL DEVICES HAVING COFIRE CERAMIC MODULES AND METHODS OF FABRICATING THE SAME

TECHNICAL FIELD

The subject disclosure relates generally to an implantable medical device (IMD) and, more particularly, to an IMD having a cofire ceramic module (CCM).

BACKGROUND

IMDs regularly provide functions for physiological health that are of critical importance in maintaining life as well as quality of life. For example, implantable pacemakers can deliver electrical pulses to the heart of the wearer of the IMD to maintain the heart beat at a normal rate. As another example, an implantable defibrillator can deliver electrical energy to the heart of the wearer of the IMD upon detection of ventricular fibrillation, cardiac dysrhythmia or pulseless ventricular tachycardia to increase likelihood of the heart returning to a normal sinus rhythm. As another example, an implantable neurostimulator can deliver electrical energy to the nervous system to reduce pain of the wearer of the IMD. As another example, an implantable deep brain stimulation device can deliver electrical energy to the brain upon detection of symptoms of neurological movement disorders to increase likelihood of return to greater physiological muscle control.

Medical care providers can monitor the IMD and assess patient current and historical physiological state to monitor the patient's condition. Providers can also initiate and modify treatment plans from time to time and/or evaluate patient compliance with nutrition, exercise and general care regiments based on data recorded in the IMD. Additionally, personnel can perform IMD diagnostics to improve function efficiencies and detection of low remaining battery life or other device or lead conditions.

Typically, patients visit a medical facility for IMD monitoring and/or retrieval of data from an IMD. Monitoring and testing of IMD data and/or modification of parameters for IMD functionality can also be facilitated remotely using one or more computer networks. For example, patient-related data can be retrieved wirelessly in some cases. In any case, the communication of information to and from the device is typically facilitated via telemetry.

Advances in technology (e.g., materials processes and integrated circuit technology) have facilitated an onslaught of the development of IMDs. However, while antennas can facilitate wireless telemetry, and thereby improve patient convenience and compliance, antenna design for IMDs presents numerous difficulties. Size and packaging constraints are particularly stringent and challenging. As such, systems, methods and apparatus associated with IMDs that employ CCMs suited to telemetry functions are desired.

SUMMARY

The following presents a simplified summary of one or more of the embodiments in order to provide a basic understanding of various aspects described herein. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include IMDs, and methods of fabricating IMDs. In some embodiments, the IMD includes a cofire ceramic module (e.g., CCM). In other embodiments, the IMD includes a housing and a CCM coupled to the housing. In either embodiment, the CCM can include an antenna cofire-integrated in the CCM. In various embodiments, the antenna can include a plate composed of conductive material, and a plurality of layers of conductive antenna elements (e.g., traces) formed as annular substrates having perimeters substantially coextensive with the perimeter of the plate. The antenna can also include a first set of one or more interconnections between the conductive plate and the conductive antenna element of one of the plurality of layers of conductive antenna elements. The antenna can also include a second set of interconnections between the conductive antenna elements of the remainder of the plurality of layers of conductive antenna elements. In some embodiments, the interconnections are capacitive interconnections, and in other embodiments, the interconnections are via interconnections. The antenna can also include a feed line conductively coupled to the plate.

As used herein, the term "feed line" or "feedthrough" means a conductive structure configured to conductively couple one component (e.g., antenna, radio frequency (RF) device) to one or more other components (e.g., component in a housing of an IMD). In some embodiments, the feed line can be formed from one or more portions of conductive material, such as that employed to form the above-described vias. In other embodiments, the feed line can include a feed line conductivity portion adapted to facilitate conductivity. The feed line conductivity portion can be surrounded by insulative material. The feed line can provide an electrically conductive path from the antenna of the CCM to the component in the housing of the IMD. For example, one embodiment can include a feed line having a first portion cofire-integrated in the CCM and having a second portion coupled to the first portion and located external to a periphery of the CCM can be included.

In some embodiments of the CCMs described herein, the CCM can also include a metal pad cofire-integrated in the CCM, and configured to provide conductivity between the antenna and a communication module. For example, the metal pad can be conductively coupled to feed line to provide conductivity between the antenna and one or more components of a housing of an IMD.

In another embodiment, a CCM includes a housing composed of dielectric material, and an antenna cofire-integrated in the housing. The antenna can include a conductive plate formed in a first configuration; and a plurality of layers of conductive antenna elements, the plurality of layers of conductive antenna elements being annular substrates formed in a second configuration, wherein the second configuration has a boundary that is substantially the same as a boundary for the first configuration. The antenna can also include a plurality of interconnections. The plurality of interconnections include: a first set of interconnections coupled between the conductive plate and the conductive antenna element of one of the plurality of layers of conductive antenna elements; and a second set of interconnections coupled between the conductive antenna elements of the remainder of the plurality of layers of conductive antenna elements. The antenna can also include a feed line coupled to the conductive plate.

In another embodiment, a method of fabricating an IMD includes: providing a plurality of first dielectric structures; forming a plurality of second dielectric structures based, at least, on providing a plurality of apertures in each of the plurality of first dielectric structures; and forming two or more conductive dielectric structures. In some embodiments, forming the two or more conductive dielectric structures includes, for at least two of the plurality of second dielectric structures: filling one or more of the plurality of apertures with first conductive material; and depositing, over one or more of the plurality of filled apertures, second conductive material, wherein the second conductive material is formed in a substantially annular-shaped configuration. In some embodiments, forming the two or more conductive dielectric structures also includes: depositing, on one or more of the plurality of filled apertures, third conductive material, wherein the third conductive material provides a plurality of interconnections; and depositing fourth conductive material associated with a feed line. The method can also include forming a laminated structure based on laminating the two or more conductive dielectric structures; and forming a CCM having a cofire-integrated antenna with cofire-integrated interconnections and the feed line based, at least, on cofiring the laminated structure.

In yet another embodiment, another method of fabricating an IMD includes: forming a laminated structure based on laminating a plurality of layers of dielectric material. In some embodiments, each of the layers of dielectric material includes: a plurality of apertures filled with first conductive material; and second conductive material provided over one or more of the filled apertures, wherein the second conductive material is formed in a substantially annular-shaped configuration. In some embodiments, each of the layers of dielectric material also includes: third conductive material provided over one or more of the filled apertures associated with a plurality of interconnections; and fourth conductive material associated with a feed line. The method can also include forming a CCM having a cofire-integrated antenna with cofire-integrated interconnections and the feed line based, at least, on cofiring the laminated structure.

Embodiments described herein can employ cofire ceramic technology to generate CCMs that facilitate telemetry to/from IMDs. The use of ceramic materials can enable fabrication of substantially RF transparent, mechanically rigid structures having small size profiles desired for implantable devices. These substantially RF transparent structures can facilitate communication of RF signals through the structures without substantial shielding or signal attenuation. Moreover, placement of components within the CCM can further reduce the size of the IMD since the number of components within the housing of the IMD can be reduced. Finally, embodiments having capacitive interconnections can provide for a reduced CCM wall thickness (and facilitate corresponding reduced antenna volume) relative to embodiments having through hole via interconnections.

Toward the accomplishment of the foregoing and related ends, the one or more embodiments can include the aspects hereinafter described and particularly pointed out. The following description, claims and annexed drawings set forth herein detail certain illustrative aspects of one or more of the embodiments. These aspects are indicative, however, of but a few of the various ways in which the principles of various embodiments can be employed, and the described embodiments are intended to include all such aspects and their equivalents.

DETAILED DESCRIPTION

Figure 1:
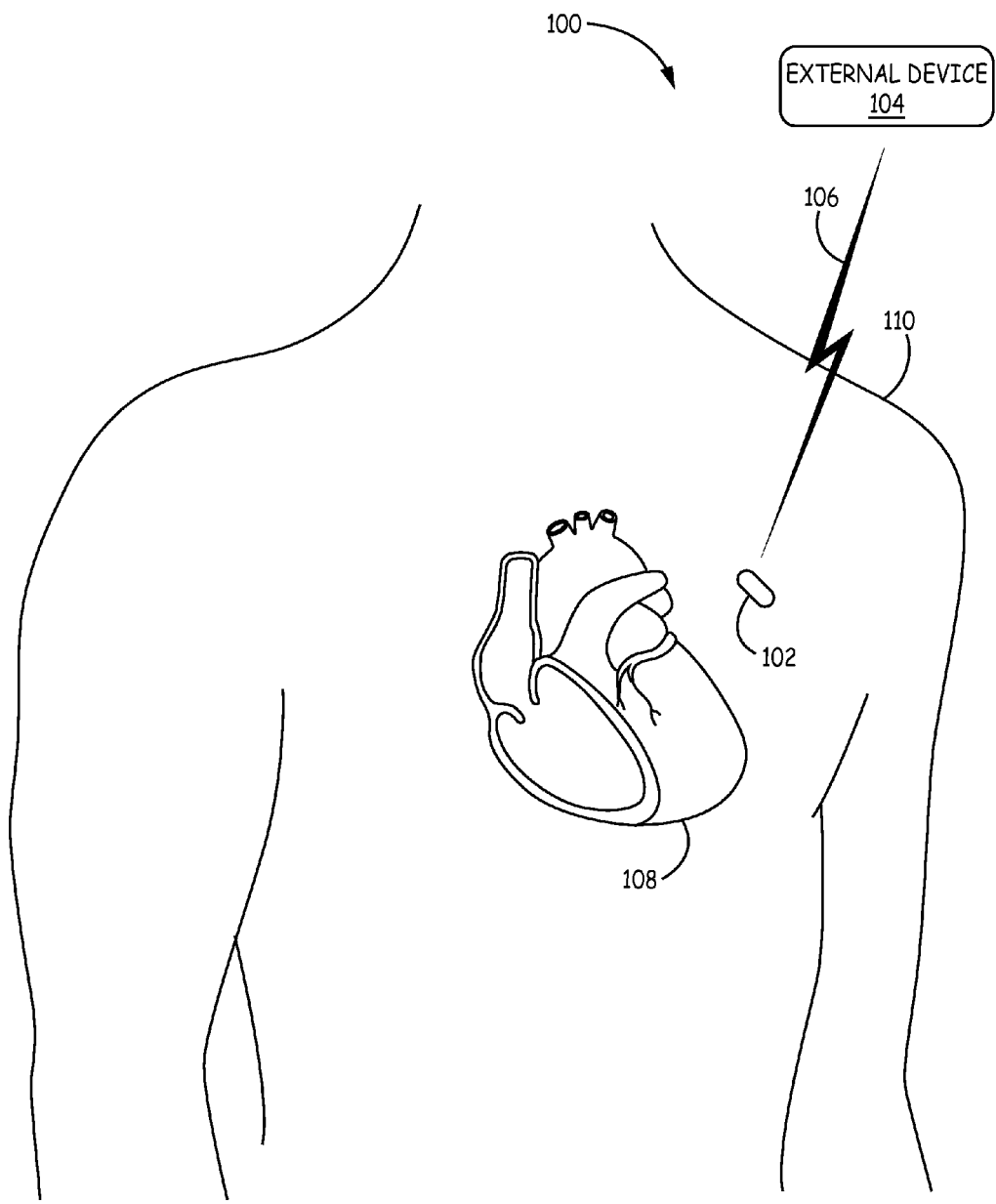
FIG. 1 illustrates a schematic diagram of an exemplary non-limiting medical device telemetry system including an external device and an IMD with CCM having cofire-integrated antenna in accordance with one or more embodiments described herein.

The following detailed description is merely illustrative and is not intended to limit embodiments or application and uses of embodiments. Furthermore, there is no intention to be bound by any expressed or implied theory presented in the preceding Technical Field, Background or Summary sections, or in the instant Detailed Description section.

One or more embodiments are now described with reference to the drawings, wherein like reference numerals are used to refer to like elements throughout. In the following description, for purposes of explanation, numerous specific details are set forth in order to provide a more thorough understanding of the various embodiments. It is evident, however, that the various embodiments can be practiced without these specific details.

Additionally, the following description refers to components being "connected," "coupled," "attached" and/or "adjoined" to one another. As used herein, unless expressly stated otherwise, the terms "connected," "coupled," "attached" and/or "adjoined" mean that one component is directly or indirectly connected to another component, mechanically, electrically or otherwise (e.g., via seal). Thus, although the figures may depict example arrangements of components, additional and/or intervening components may be present in one or more embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

Turning now to the figures, FIG. 1 illustrates a schematic diagram of an exemplary non-limiting medical device telemetry system 100. Medical device telemetry system 100 includes IMD 102 and external device 104 communicatively coupleable to IMD 102 via wireless channel 106.

IMD 102 can perform any number of functions for detection and/or treatment of medical conditions. For example, in one embodiment, IMD 102 can be a subcutaneous sensing device configured to sense signals indicative of one or more physiological parameters of human body 110. IMD 102 can be an insertable cardiac monitor configured to sense and/or store electrocardiogram (ECG) signals. In some examples, IMD 102 can be configured to sense ECG or other signals and detect arrhythmias, e.g., ventricular and/or supra-ventricular arrhythmias, based on the signals. In other instances, IMD 102 can alternatively or additionally be configured to deliver therapy to human body 110.

FIG. 1 further depicts external device 104 in communication with IMD 102 via wireless channel 106. In some examples, external device 104 comprises a handheld computing device, programmer, computer workstation, or networked computing device. External device 104 can include a user interface that presents information to and facilitates receipt of input from a user (e.g., physician). It should be noted that the user can also interact with external device 104 remotely via a networked computing device.

A user, such as a physician, technician, surgeon, electrophysiologist, other clinician, or patient, interacts with external device 104 to communicate with IMD 102. For example, the user can interact with external device 104 to retrieve physiological or diagnostic information from IMD 102. A user can also interact with external device 104 to program IMD 102, e.g., select values for operational parameters of the IMD 102. For example, the user can use external device 104 to retrieve information from IMD 102 regarding the rhythm of heart 108, trends therein over time, or arrhythmic episodes.

IMD 102 and external device 104 can communicate via wireless communication using various techniques known in the art. Examples of communication techniques can include, for example, low frequency or RF telemetry, proximal inductive telemetry (e.g., via magnetic field coupling), or tissue conductance communication, but other techniques are also contemplated. In some examples, external device 104 can include a programming head that can be placed proximate to or in contact with the patient's body near an implant site for IMD 102 to improve quality or security of communication between IMD 102 and external device 104.

External device 104 can be or include any type of device configured to process, store, display, analyze and/or test medical device telemetry data. For example, external device 104 can include, but is not limited to, a personal computer, laptop, smart phone or the like. In various embodiments, external device 104 can include programs, modules, hardware, software and/or computer-readable storage media to facilitate monitoring, testing, analyzing, processing, storage and/or display of data associated with information retrieved from IMD 102. In various embodiments, one or more of external device 104 can include, or be communicatively coupled to, a receiver (not shown) configured to receive signals from antenna 302. External device 104 can be communicatively coupled to a transmitter and antenna configured to transmit information to antenna 302.

In some embodiments, external device 104 can transmit information to IMD 102 to update operation of IMD 102. By way of example, but not limitation, external device 104 can transmit information to cause an update in parameter values to change operation of IMD 102. In particular, the information transmitted from external device 104 to IMD 102 and/or a processor of IMD 102 can cause a modification in operation of IMD 102.

As will be described in further detail herein, IMD 102 includes a CCM that includes a cofire-integrated antenna in accordance with one or more embodiments described herein. The CCM can, in various instances, be a header of IMD 102. The header can be formed separately from the housing of IMD 102 and attached during assembly of IMD 102. Further, in some embodiments, a second housing can encapsulate the CCM, or a cap can cover the portion of the CCM open to human body 110. In addition to an antenna, CCM can further integrate other components, such as an integrated circuit (IC), RF chip or a passive network (or capacitor or inductor of a passive network, for example). In other instances, CCM may be a component that is integrated within a header of a device, but not function as the header.

Figure 2:
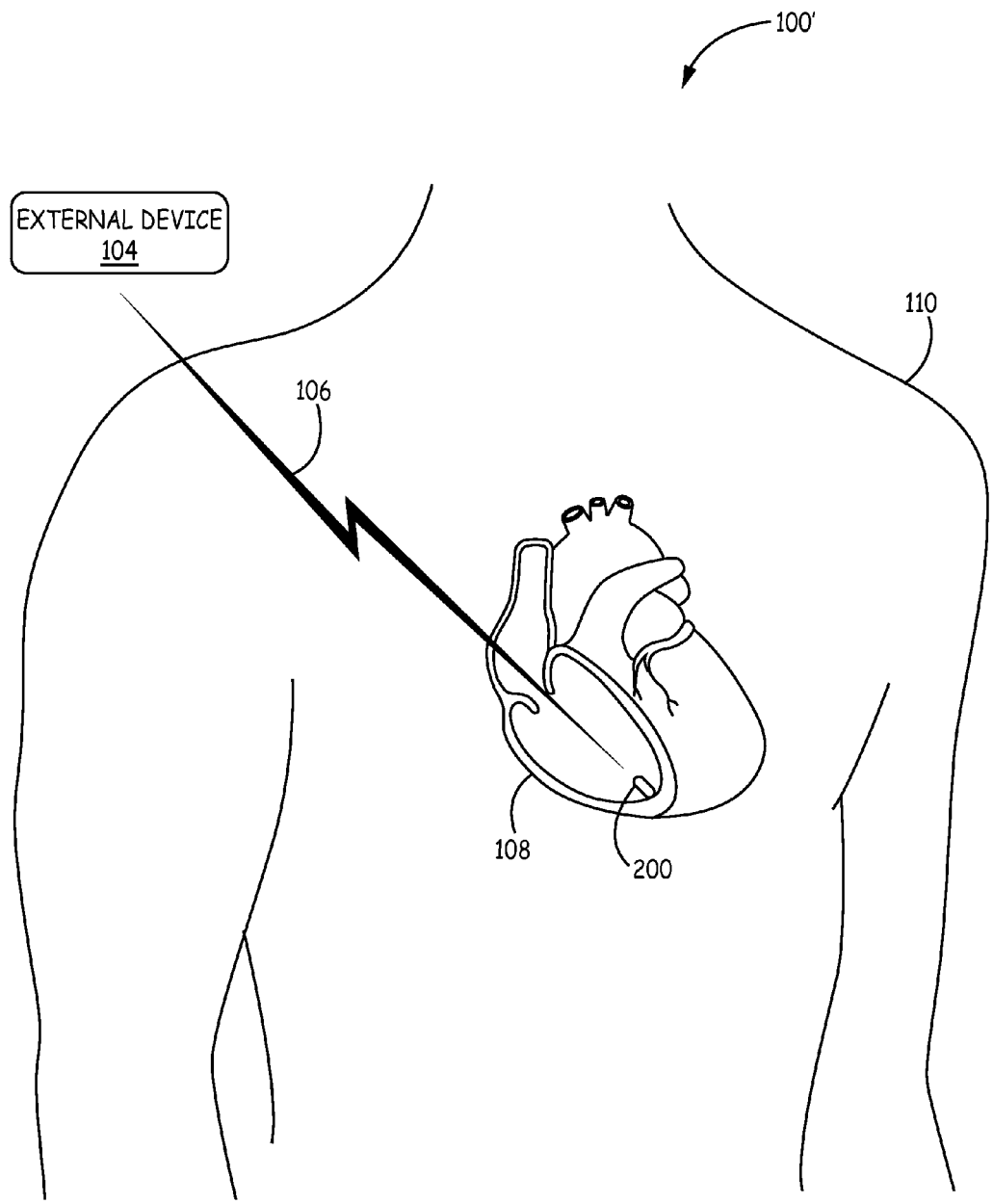
FIG. 2 illustrates a schematic diagram of another exemplary non-limiting medical device telemetry system including an external device and an IMD with CCM having cofire-integrated antenna in accordance with one or more embodiments described herein.

FIG. 2 is a schematic diagram illustrating another exemplary medical device telemetry system 100'. In various embodiments, system 100' can include one or more of the structure and/or functionality of system 100 (and vice versa). Repetitive description of like elements employed in other embodiments is omitted for sake of brevity.

Medical device telemetry system 100' conforms substantially to system 100 of FIG. 1 in structure and/or function, except IMD 200 is or includes an implantable leadless IMD (e.g., implantable leadless pacemaker) implanted within a ventricle of heart 108 of human body 110. IMD 200 includes one or more electrodes (not illustrated in FIG. 2) via which IMD 200 provides electrical stimulation to the ventricle of heart 108 of human body 110, such as one or more pacing pulses. Additionally or alternatively, IMD 200 can sense electrical signals attendant to the depolarization and repolarization of the heart 108 via the one or more electrodes. In one example, IMD 200 provides therapy to human body 110 based on sensed physiological signals.

Although IMD 102 of FIG. 1 is illustrated as being implanted subcutaneously in a left pectoral region of human body 110 and IMD 200 of FIG. 2 is illustrated as being implanted within a left ventricle of heart 108, IMD 102 and/or IMD 200 can be implanted in other locations. For example, IMD 200 can be positioned within any suitable region of human body 110, such as within an atrium of heart 108 or at an epicardial location of heart 108. In some examples, depending on the location of implant, IMD 200 can include other sensing and/or stimulation functionalities. In some examples, system 100' can include a plurality of leadless IMDs 200, e.g., to provide stimulation and/or sensing at a variety of locations.

Although the examples described herein generally refer to a leadless IMD, in some embodiments, IMD 102 and/or IMD 200 can alternatively be coupled to one or more leads including one or more electrodes configured to sense the one or more physiological parameters of human body 110 and/or to deliver therapy to heart 108 of human body 110. Moreover, although described generally as cardiac IMDs, the CCMs described herein may be used within other implantable devices including, but not limited to, neurological devices, drug pumps, or other implantable devices.

Figure 3:
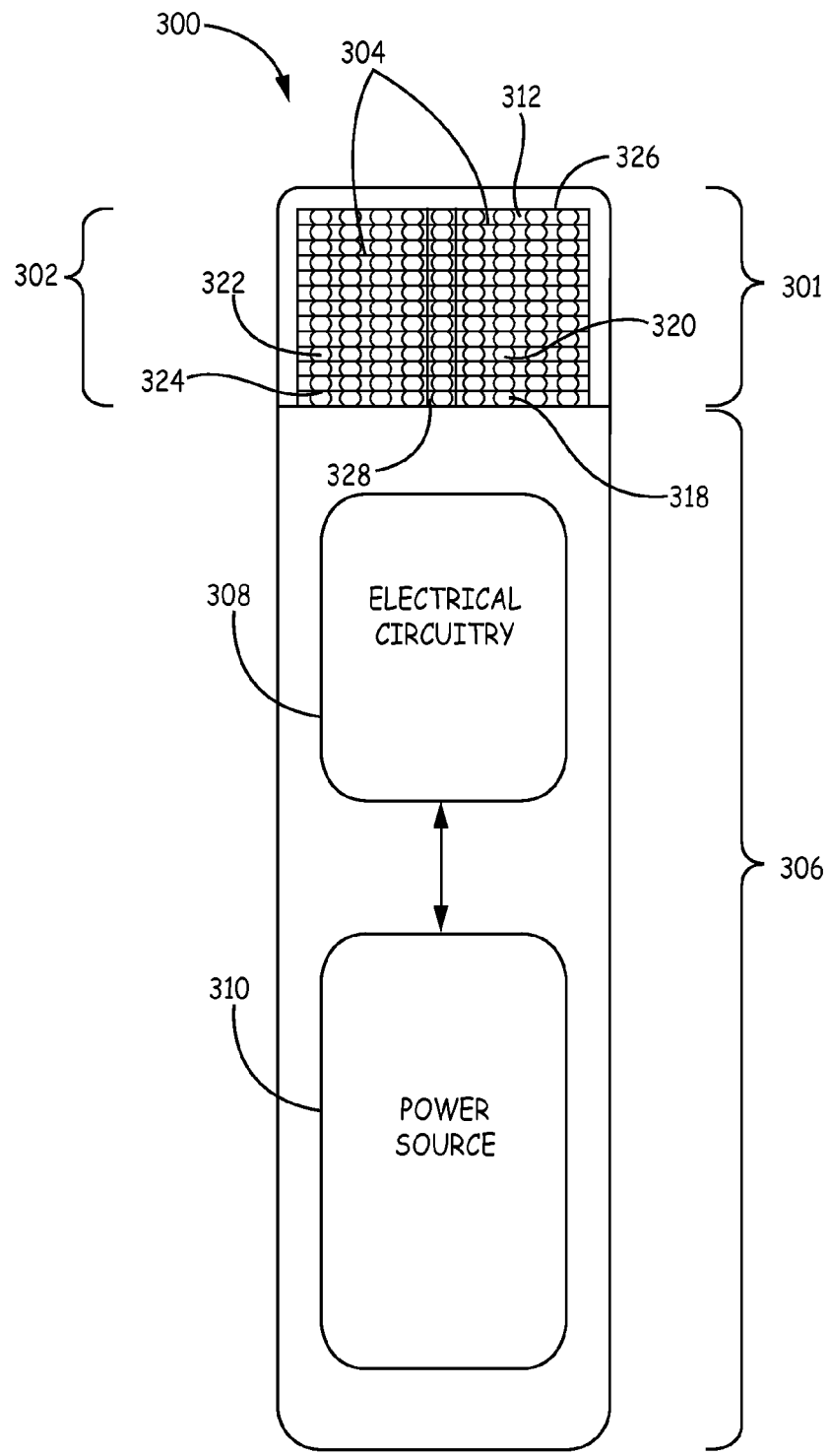
FIG. 3 illustrates a cross-sectional view of an exemplary non-limiting IMD having a CCM and cofire-integrated antenna with columnar feed line in accordance with embodiments described herein.

FIG. 3 illustrates a cross-sectional view of an exemplary non-limiting IMD having a CCM and cofire-integrated antenna with columnar feed line in accordance with embodiments described herein. In various embodiments, IMD 300 can include one or more of the structure and/or functionality of IMD 102, 200 (and vice versa). Repetitive description of like elements employed in other embodiments is omitted for sake of brevity.

As shown, IMD 300 can include housing 306 and CCM 301 having cofire-integrated antenna 302 embedded in CCM 301. IMD 300 can also include electrical circuitry 308 and/or power source 310 configured to power IMD 300 and located in housing 306. In various embodiments, one or more of CCM 301, cofire-integrated antenna 302 cofire-integrated in CCM 301, housing 306, electrical circuitry 308 and/or power source 310 can be communicatively and/or electrically coupled to one another to perform one or more functions of IMD 300.

Antenna 302 can be disposed within dielectric material 312 as shown in FIG. 3. In various embodiments, various components of antenna 302 can be formed by depositing, into one or more apertures in dielectric material 312, material from the component is composed, laminating the structure and cofiring the structure to form the CCM 301. In some embodiments, antenna 302 can include conductive plate 326 conductively coupled to a plurality of conductive antenna elements (e.g., traces) 304, and intervening interconnections forming side walls of antenna 302.

In various embodiments, conductive plate 326 can be fabricated to be a top planar component of antenna 302 while the bottom portion of antenna 302 proximate to housing 306 can be open, without a conductive plate. In various embodiments, each conductive antenna element 304 can be formed in the configuration of an annular substrate having a perimeter substantially equal to the perimeter of conductive plate 326. The shape of the annular substrate of conductive antenna elements 304 can be substantially the same as the shape of conductive plate 326 (e.g., rectangular, square, oval, circular, irregular) in various embodiments depending on the design radiation pattern and performance of antenna 302. In the embodiment shown, conductive plate 326 and conductive antenna elements 304 are rectangular in shape and antenna 302 is rectangular prismatic.

Any number of annular substrates can be included in antenna 302 based on the desired dimensions of the antenna and/or corresponding performance. Each trace 304 is substantially vertically aligned (e.g., stacked formation) below conductive plate 326 with intervening interconnections (e.g., interconnections 318, 320, 322, 324) providing antenna 302 sidewalls such that antenna 302 is a three-dimensional antenna formed in a substantial cage-shaped formation having a closed top and an open bottom.

In the embodiment shown, exemplary interconnections 318, 320, 322, 324 are shown for purposes of illustration only as the number and location of interconnections can vary as determined by the desired performance of antenna 302. In some embodiments, a first set of interconnections is conductively coupled between conductive plate 326 and a layer of a trace 304, and a second set of interconnections is conductively coupled between two or more layers of traces 304.

Antenna 302 can also include feed line 328 conductively coupled to conductive plate 326 and provided through dielectric material 312 to a portion of antenna (and CCM 301) proximate to housing 306. For example, one or more portions of feed line 328 can be cofire-integrated in antenna 302. In the embodiment shown, feed line 328 is formed in a columnar configuration; however, in other embodiments (as shown with reference to FIG. 5), a substantially serpentine-shaped feed line (feed line 504) can be provided to adjust impedance in antenna 302. In any embodiment, the feed line can provide conductivity between the antenna and/or CCM and a component outside of the CCM (e.g., a component of housing 306).

In various embodiments, feed line 328 can be composed of material from which interconnections are composed. For example, in the embodiment shown, feed line 328 can be composed from conductive material from which vias are composed and can be provided in the form of a continuing via across the numerous layers of dielectric 312 of CCM 301.

While the embodiment illustrated in FIG. 3 is a cross-sectional view, as described herein, antenna 302 is a three-dimensional antenna. As such, the configuration of antenna 302 can be a three-dimensional configuration across numerous regions within CCM 301. In various embodiments, antenna 302 can be designed to have different radiation patterns, materials and/or parameters to facilitate radiation of electromagnetic energy with different devices and/or in different environments. For example, in various embodiments, conductive plate 326 and conductive antenna elements 304 can be formed in any number of different configurations.

Further, while the embodiment illustrated in FIG. 3 includes only one three-dimensional antenna, in other embodiments, more than one three-dimensional antenna can be integrated into a single CCM via the cofiring process. For example, two or more antennas can be cofire-integrated into CCM 301. The antennas can be formed in different configurations and can receive and/or transmit signals having different wave patterns, frequencies, polarities, or other different characteristics to provide for antenna diversity. As such, depending on the external device to which antenna 302 is communicating in a particular environment, which can change from time to time, multiple antennas cofire-integrated into a single CCM can be employed for communication.

Antenna 302 can be configured to transmit and/or receive information to and/or from external device 104, which is illustrated in FIGS. 1 and 2. By way of example, but not limitation, antenna 302 can transmit information indicative of a biological event of a human body 110, current and/or historical data generated by IMD 300, remaining battery life of IMD 300 and/or diagnostic information associated with functionality and/or operation of IMD 300. By way of other examples, but not limitation, antenna 302 can receive from external device 104 information indicative of one or more parameter values by which IMD 300 operates. The information can be received at IMD 300 and/or electrical circuitry 308 of IMD 300 and cause IMD 300 to modify parameter values by which IMD 300 operates.

In various embodiments, antenna 302 can transmit and/or receive information indicative of past or current activity (e.g., heart rhythms, heart rate, arterial blood oxygen saturation, cardiac output, intravascular pressures, blood pressure, blood temperature, blood oxygen level, heart electrical activity, brain electrical activity, level of quinolinic acid, neurotransmitters, nerve activity, nerve-muscle activity or spinal cord nerve activity). In some embodiments, antenna 302 can transmit and/or receive information indicative of past or current events (e.g., heart attacks, heart failure, arrhythmias, unrecognized myocardial infarctions, chronic pain nerve signals, brain aneurysms, neurological injury, stroke, brain injury).

In some embodiments, antenna 302 can transmit and/or receive information to cause IMD 300 to perform any number of functions including, but not limited to, outputting electrical signals to one or more organs, muscles, nervous system and/or spinal cord in human body 110, brain stimulation, interruption of pain signals, spinal cord stimulation, monitoring and/or sensing activity of one or more organs in human body 110 and/or monitoring and/or identification of defined chemicals (or levels of defined chemicals) in human body 110.

In some embodiments, electrical circuitry 308 can include one or more components or modules configured to perform an electrical function. By way of example, but not limitation, electrical circuitry 308 can include a communication module (e.g., transmitter, receiver and/or transceiver) configured to output a signal to a body of a wearer of IMD 300, sensing module configured to sense a physiological or biological signal of human body 110, a therapy module configured to generate and deliver an electrical stimulation therapy to human body 110 or to generate a signal causing IMD 300 to output medication to the body of the wearer of IMD 300 or the like. In various embodiments, electrical circuitry 308 can include circuitry for one or more of an implantable sensor, an implantable therapy lead, an implantable sensor, an implantable monitor, an implantable cardioverter defibrillator, an implantable neurostimulator, an implantable physiological monitor and/or an implantable pulse generator. Sensors described herein can include sensors of different organs and physiological components including, but not limited to, lung, spine, eyes, heart, brain and/or nerve sensors.

With reference to FIGS. 1 and 3, IMD 300 can be subcutaneously implanted within skin, fat and/or muscle of human body 110, swallowed and/or injected into the bloodstream of human body 110. Further, shown is human body 110; however, CCM 301 can also be provided within other types of structures (e.g., animal body) in various embodiments.

CCM 301 can be electrically coupled and/or communicatively coupled to electrical circuitry 308 such that communication circuitry is electrically coupled and/or communicatively coupled to antenna 302. For example, electrical and/or communicative coupling can occur via feed line 328 of antenna 302. By way of example, but not limitation, electrical circuitry 308 can include one or more of an RF module, a controller, a processor, a memory, data storage or the like. As such, one or more operations of medical device telemetry system 100, 102' and/or of the embodiments of IMDs described herein can be facilitated.

IMD 300 can be an implantable device configured to output an electrical signal to human body 110 and/or monitor fluid, nerves, organ activity and/or other physiological condition (e.g., level of cholesterol, level of serotonin) of human body 110. Examples of IMD 300 can include, but is not limited to, pacemakers, implantable neurostimulators, implantable cardioverter defibrillators, implantable physiological monitors and/or implantable therapy leads.

As shown, antenna 302 can be completely encapsulated within the walls of CCM 301 in various embodiments. Dielectric material 312 from which CCM 301 is formed can electrically isolate antenna 302 from housing 306 (which, in some embodiments, can be formed of metal). In various embodiments, if CCM 301 is composed of a biocompatible material, CCM 301 can be exposed to bodily tissues and fluids as no cap is needed over CCM 301.

In some embodiments, CCM 301 can be directly joined to housing 306 with no additional components (e.g., device headers, caps). However, in such embodiments, CCM 301 can be encapsulated in housing 306 in lieu of being adjoined to housing 306. Accordingly, housing 306 can shield the body from CCM 301 thereby minimizing leakage of materials from, and/or body fluid ingress into, CCM 301 and/or antenna 302. Placing CCM 301 inside housing 306 can also minimize body immune response to CCM 301 (in embodiments in which housing 306 is composed of biocompatible and/or biostable materials).

Housing 306 can be a polymeric housing and can thereby be biostable and/or biocompatible in some embodiments. In various embodiments, housing 306 and CCM 301 are adjoined to one another. For example, in some embodiments, housing 306 and CCM 301 are adjoined to one another via a seal. In some embodiments, the seal is a hermetic seal. In some embodiments, housing 306 and CCM 301 are individually hermetically sealed and then adjoined to one another. The hermetic seal can be provided via any number of methods for providing hermetic seals including, but not limited to, brazing, soldering, welding, compression sealing, glass sealing, diffusion bonding and/or epoxy sealing. In some embodiments, a conductive material can be cofired around the edges of CCM 301. The conductive material can then be welded to housing 306 in some embodiments.

In some embodiments, one or more seals employed can be non-hermetic seals (e.g., plastic encapsulation). For example, in embodiments in which CCM 301, antenna 302 and feed line 328 of antenna 302 and/or IMD 300 are composed of biostable and biocompatible materials and/or in which housing 306 and CCM 301 are individually hermetically sealed, housing 306 and CCM 301 can be adjoined by a non-hermetic seal.

In various embodiments, housing 306, or one or more components of housing 306, can be electrically coupled to CCM 301, including coupling to antenna 302, capacitively (as described with reference to FIGS. 8 and 9A-9E) or via feed line 328 to perform one or more functions of components of housing 306 and/or CCM 301. For example, operations of antenna 302 can be facilitated via capacitive or electrical coupling between CCM 301 and components of housing 306. In some embodiments, housing 306 (or a component of housing 306), antenna 302 and/or CCM 301 can be electrically coupled to one another via feed line 328.

As shown, CCM 301 is not encapsulated by a housing and, as such, upon implantation, is in direct contact with human body tissue and/or human body fluid. As such, in some embodiments, CCM 301 and/or antenna 302 can be composed of biostable and/or biocompatible materials. In some embodiments, biostable and/or biocompatible material can be employed for the outermost layer of materials from which CCM 301 and/or antenna 302 are formed. As such, portions of CCM 301 and/or antenna 302 most likely to contact human body issue and/or human body fluid can be composed of biostable and/or biocompatible material.

Figure 4A:
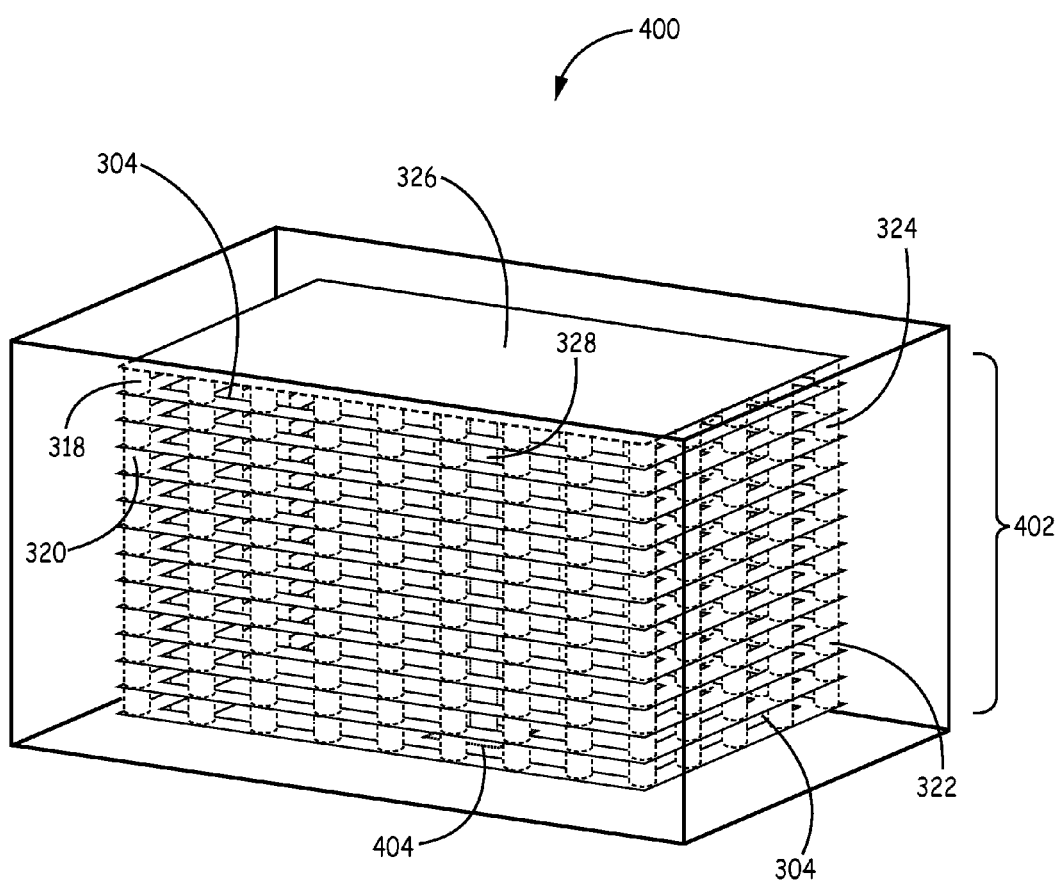
FIG. 4A illustrates a perspective view of an exemplary non-limiting CCM having a cofire-integrated antenna with columnar feed line in accordance with embodiments described herein.

Antenna 302 can be further described with reference to FIGS. 4A-4G. Turning first to FIG. 4A, illustrated is a perspective view of an exemplary non-limiting CCM having a cofire-integrated antenna with columnar feed line in accordance with embodiments described herein. In various embodiments, CCM 400 can include one or more of the structure and/or functionality of CCM 301 (and vice versa). Also, antenna 302 can include one or more of the structure and/or functionality of antenna 402 (and vice versa). Repetitive description of like elements employed in other embodiments is omitted for sake of brevity.

Antenna 402 is cofire-integrated into CCM 400. CCM 400 can be formed, for example, according to a fabrication process described below. After cofiring, for example, CCM 400 can include dielectric material 312 with an embedded conductive plate 326, and multiple layers of conductive antenna elements (e.g., traces) 304 having a generally annular configuration and vertically aligned relative to one another. In some embodiments, intervening interconnections can be provided between the conductive plate 326 and a first layer of conductive antenna element 304, and between two or more layers of conductive antenna elements 304. In the embodiments shown and described with reference to FIGS. 3 and 4A-4G, described herein, interconnections can be via interconnections.

Interconnections 318, 320, 322, 324 are examples of the embodiments of the configurations and locations of interconnections. While the interconnections are shown in a first set of positions, as described, in other embodiments, the interconnections can be provided in other locations and/or configurations. As shown in FIG. 4A, interconnections are provided between every set of conductive antenna elements 304 and between the conductive plate 326 and conductive antenna element 304 adjacent conductive plate 326 to provide desired conductivity across the regions of antenna 304 (and across regions of CCM 400).

By way of example, but not limitation, one or more apertures for interconnections and/or conductive antenna elements can be placed in one or more layers of dielectric material 312 that will form CCM 400 post-cofiring. The apertures can be provided at positions corresponding to desired locations of interconnections that will provide electrical connection across antenna 402 between the layers of dielectric material 312. For example, as show in FIG. 4A, antenna 402 includes interconnections (e.g., interconnections 318, 320, 322, 324) along the periphery of layers of dielectric material 312, and forming side walls of, antenna 402, such that the interconnections are provided in the y axis of one or more layers of dielectric material 312. The conductive material can be deposited via screen printing in some embodiments.

Antenna 402 can also include feed line 304 provided from conductive plate 326 (proximate to a first end of antenna 402) to a region of antenna 402 proximate to the second end of antenna 402. In some embodiments, apertures can be provided in various layers of dielectric material 312 at which feed line 328 is desired post-cofiring. Conductive material from which via interconnections can be formed can be provided in the apertures to result in the feed line 328 from conductive plate 326 through numerous regions of CCM 400 and antenna 402. As such, feed line 328 can provide conductivity between antenna 302 and one or more components outside CCM 400.

In various embodiments, CCM 400 can include metal pad 400. Metal pad 404 can be cofire-integrated into CCM 400 such that it is provided on an exterior surface of CCM 400. For example, prior to cofiring, conductive material from which metal pad 404 is composed can be provided on a side of at least one layer of dielectric material 312 of CCM 400 that will be an external surface of CCM 400 after cofiring. As such, metal pad 404 can be provided on a bottom, exterior surface of CCM 400 between CCS 400 and a housing that can be adjoined to CCS 400. In various embodiments, metal pad 404 is formed in different configurations and/or sizes.

Feed line 328 can be provided on an interior surface of CCM 400 at a location corresponding to the location of metal pad 404. Accordingly, metal pad 404 can be electrically coupled to feed line 304. By way of example, but not limitation, in some embodiments, metal pad 404 can be configured to electrically couple to a wire or other component configured to transmit electricity between a component outside of CCM 400, metal pad 404 and/or feed line 328. In various embodiments, whether metal pad 404 is electrically coupled to feed line 328 and/or the size of metal pad 404, can be a design choice based on the size of CCM 400, access to feed line 328, the interconnect method between metal pad 404, and feed line 328 and/or any number of other considerations.

Further, the interconnect method between metal pad 404 and feed line 328 can be at least partially dictated by whether a biocompatible metal pad is desired. For example, if CCM 400 is located outside of a hermetically sealed housing, a biocompatible and biostable metal pad is desired. The interconnection method can be one that can provide a biocompatible connection between metal pad 404 and CCM 400 that is not likely to corrode over time (e.g., welding).

Welding can be employed in conjunction with metals that are stable in aqueous/body fluid environments, for example. Examples of such metals include, but are not limited to, niobium, platinum, stainless steels and titanium.

Any number of welding techniques can be employed to form hermetic joints between metal pad 404 and feed line 328, for example. Welding techniques for providing a biocompatible and biostable include, but are not limited to, those using heat sources, such as parallel gap welding, laser welding or otherwise joining with a laser (e.g., laser brazing, laser soldering, laser chemical reaction, laser softening of glue), opposed gap welding, step gap welding, diffusion bonding (pressure and temperature), braze or solder in a furnace, braze or solder with resistance heating, braze or solder with a laser, ultrasonic bonding, weld/ball/ribbon welding, reaction welding, sintering, and exothermic reaction of a multilayer stack. Mechanical joining techniques for establishing an electrical contact can include scraping, pressure contact, and pin and socket.

In some embodiments, an interposer (e.g., a platinum pad of a cofire feed line pad or pad array) can be joined to feed line 328. In various embodiments, the interposer can be, but is not limited to, thin film, thick film, blocks, lead frames, stack of cofire components joined with gold braze or platinum-sintered cofire pads (or of other alloys such as platinum-iridium or other nano-sized particles of refractory biostable, biocompatible metals such as platinum, titanium, tantalum, niobium, gold, and alloys and oxides thereof).

In some embodiments, a conductive lead (e.g., platinum, platinum-iridium alloy, titanium, tantalum, niobium, gold, and alloys and oxides thereof) can be subsequently welded to the interposer using a variety of joining techniques to form a hermetic joint of the interposer to feed line 328.

Joining techniques for providing a biocompatible and biostable joint include, but are not limited to, those using heat sources, diffusion bonding (pressure and temperature), brazing or soldering in a furnace, brazing or soldering with resistance heating, brazing or soldering with a laser or otherwise joining with a laser, ultrasonic bonding, reaction welding, and exothermic reaction of a multilayer stack. In some embodiments, hybrid approaches that combine joining techniques can be used to form a hermetic joint of a lead to feed line 328.

In some embodiments, parallel gap welding of a lead formed from an alloy (e.g., alloy including nickel, cobalt, and chromium) to a platinum pad can be conducted without damaging hermeticity of the joint between metal pad 404 and feed line 328 by using a current of less than 0.5 kiloamperes (kA) (e.g., about 0.13 kA), a force of less than five pounds per electrode (e.g., about 2 lb. force/electrode), using copper-based metal matrix composite alloy electrodes (e.g., sized about 0.015 by about 0.025 inch), and in an inert cover gas (e.g., argon, helium, nitrogen, etc.).

The thickness of metal pad 404 on CCM 400 can be at least about 3 milli-inches (mils) to provide adequate thermal isolation of the underlying brittle ceramic from the input weld energy. Further, feed line 328 and/or metal pad 404 can be composed of biocompatible material such as niobium. Finally, feed line 328 can be a traditional feed line 328 in this embodiment and include a pin or ribbon making up feed line 328.

In embodiments in which CCM 400 and metal pad 404 are located within a hermetically sealed housing of the IMD, the interconnect method between metal pad 404 and CCM 400 need not be biocompatible. In particular, metal pad 404 can be formed after CCM 400 is cofired or used in its cofire condition (without further welding, for example). In this case, metal pad 404 can be a thinner platinum pad similar in structure to a surface mount soldered interconnect and can be placed on a newly-machined exterior surface of CCM 400. The thinner platinum pad can have thin film metal layers that enable the use of common solder materials and processes. In some embodiments, metal pad 404 can be cofired within CCM 400.

Accordingly, in embodiments in which metal pad 404 will not be exposed to bodily fluid or gases, the interconnect method can be any of the traditional approaches (which would tend to corrode over time if exposed to wet environments such as those inside of a human body. These interconnect methods can include, but are not limited to, surface mount methods, solder methods or wire bonding.

Turning back to FIG. 4A, while a first end at which conductive plate 326 is located closed, a second end (opposite the first end) is open. Specifically, the second end of antenna 402 is open with no conductive plate. Accordingly, the interconnections of antenna 402 can provide electrical conductivity across various regions of CCM 400 and antenna 402. As shown, antenna 402 can be composed of a series of via interconnections stacked along a y-axis and annular substrate conductive elements 304 (e.g., traces) along an x-z axis connected to form a substantially cage-shaped configuration around feed line 328 of antenna 402.

In various embodiments, different configurations of antenna 402 are possible. Accordingly, while antenna 402 is substantially rectangular prismatic in FIGS. 4A-4G, in various embodiments, any number of other configurations of three-dimensional antennas can be employed. For example, antenna 402 can be substantially cuboid in some embodiments or have an irregular three-dimensional shape in some embodiments.

The incorporation of thinner layers of dielectric material 312 and smaller diameters of the interconnections (e.g., interconnections 318, 320, 322, 324) in CCM 400 and antenna 402 can allow for significant reduction in volume of antenna 402 with only modest changes in efficiency and gain. Cofire ceramic technology can utilize dielectric layers that can vary in thickness from, for example, 25 microns (μm) to 500 um. Antenna dimensions can also be controlled. For example, very fine widths of conductive material from which antenna 402 is composed can be less than about 30 μm. Diameters of interconnections 318, 320, 322, 324 can be less than about 50 μm. The flexibility to control the dielectric thickness and composition, and conductor dimensions allows the preparation of antennas with minimum volume and high performance.

In FIG. 4A, CCM 400 is transparent to better illustrate the details of antenna 402. However, CCM 400 need not be transparent and, in some embodiments, CCM 400 can be opaque or translucent. Conductive plate 326, conductive antenna elements 304 and/or interconnections 318, 320, 322, 324 can be Platinum (Pt) in some embodiments. In this embodiment, dielectric material 312 from which CCM 400 is formed can electrically isolate antenna 402 from a housing to which CCM 400 can be coupled and which can be metal (e.g., Titanium (Ti)) in some embodiments.

Generally, the substantially cage-shaped configuration of antenna 402 is particularly practical for the cofire process since the process employs layering of different materials prior to lamination and cofiring into a single module (e.g., CCM 400). From a design perspective, antenna 402 is advantageously simple because the layers of the antenna can be the same in various embodiments. Further, as described in Table 1 below, the antenna provides desirable radiation efficiency—volume trade-off, which is particularly useful for implantation as smaller IMDs are desirable. Finally, impedance is generally advantageous relative to other antenna designs, and can be further improved with substantially serpentine-shaped configuration of feed line (as described below with reference to FIG. 5). In some embodiments, with reference to FIGS. 3 and 4A, antenna 302, 402 can effective form a slot between antenna 302, 402 and the remaining portion of IMD 300 so that antenna 302, 402 enhances radiation, especially when embedded into CCM 301, 400.

Table 1 illustrates dimensions and performance of exemplary non-limiting three-dimensional substantially cage-shaped cofire-integrated antennas without feed lines in accordance with one or more embodiments described herein.

TABLE 1

| IMD Number | Housing Case | Radiator | Header Molding | Phantom Body | Office | Re (Zin) | Im (Zin) | Radiation Efficiency (dB) | Gain (dB) |
| --- | --- | --- | --- | --- | --- | --- | --- | --- | --- |
| 1 | Ti | Pt Cage-Shaped Antenna (vias and traces) | $Al_2O_3$ | Saline | Air | 7.2 | -28.3 | -33.4 | -30.0 |
| 2 | Ti | Pt Cage-Shaped Antenna (vias and traces) | $Al_2O_3$ | Saline | Air | 6.0 | -31.7 | -33.8 | -30.6 |
| 3 | Ti | Pt Cage-Shaped Antenna (vias and traces) | $Al_2O_3$ | Saline | Air | 5.8 | -30.0 | -34.2 | -30.7 |

As described above, phantom body is composed of saline (conductivity ($\sigma$)=0.85 Siemens per meter (S/m); and dielectric constant ($\in_r$)=60); the air environment is $\in_r$=1; and the housing case is composed of Titanium (Ti) ($\sigma$=1.82×10$^6$ S/m). IMD number 2 and 3 each have an antenna with the same volume embedded in a CCM. However, the CCM for IMD number 3 has volume of 70.7 millimeters (mm)$^3$ while the CCM for IMD number 2 has volume of 88.6 mm$^3$.

As shown, with reference to Table 1, radiation efficiency of IMD number 2 is −33.8 decibels (dB) while the radiation efficiency of IMD number 3 is −34.2 dB. Accordingly, IMD number 3 has decreased volume relative to IMD number 2 with a reduction in radiation efficiency from −33.8 dB to only −34.2 dB. In various embodiments, the volume of the antenna can be further reduced dependent on impedance and efficiency constraints.

Figure 4B:
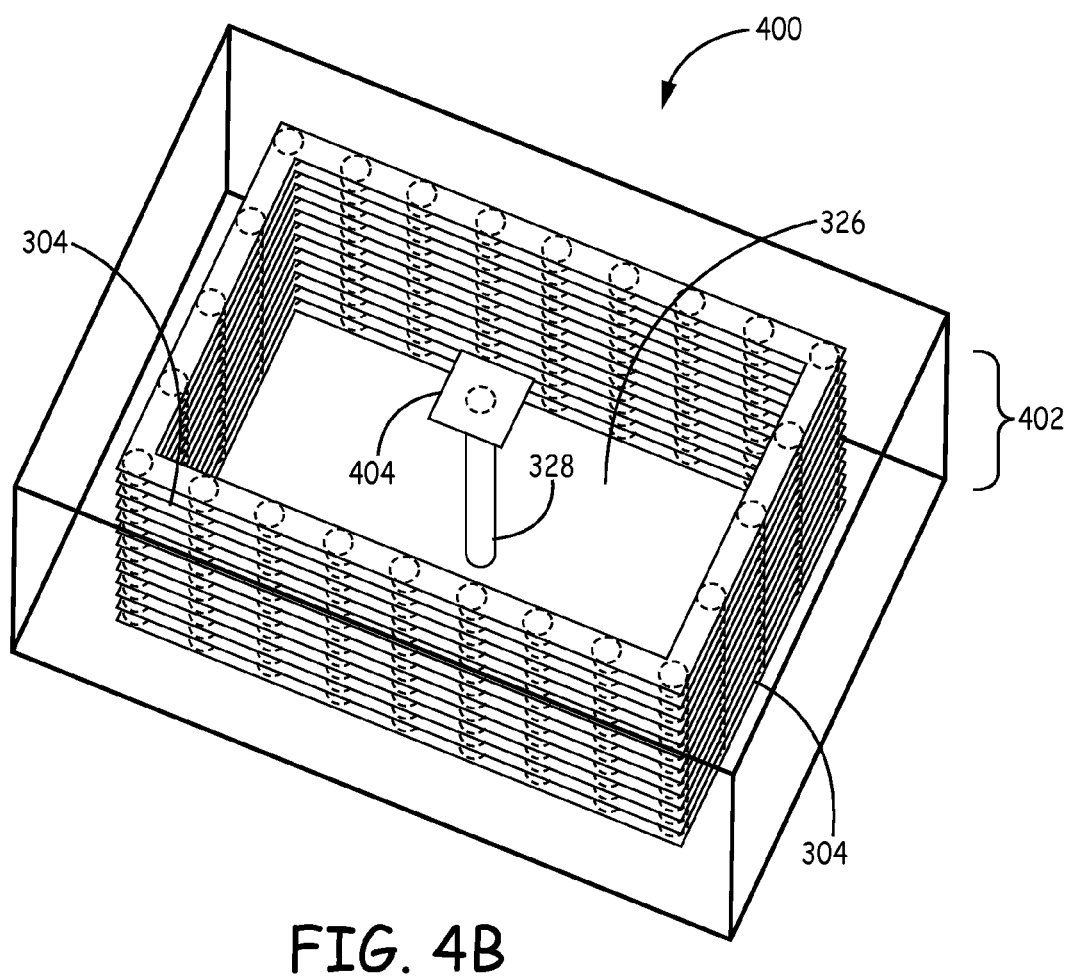
FIG. 4B illustrates another perspective view of an exemplary non-limiting CCM having a cofire-integrated antenna with columnar feed line in accordance with embodiments described herein.
Figure 4C:
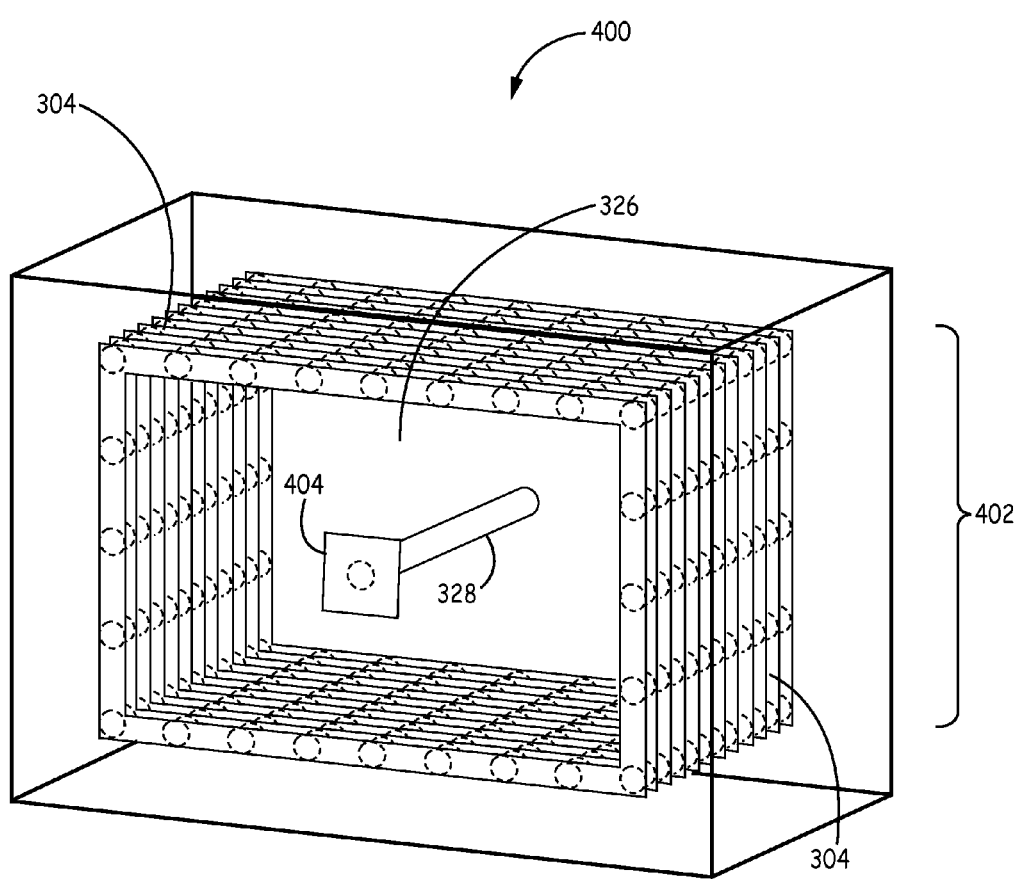
FIG. 4C illustrates another perspective view of an exemplary non-limiting CCM having a cofire-integrated antenna with columnar feed line in accordance with embodiments described herein.

FIG. 4B illustrates another perspective view of an exemplary non-limiting CCM having a cofire-integrated antenna with columnar feed line in accordance with embodiments described herein. FIG. 4C illustrates another perspective view of an exemplary non-limiting CCM having a cofire-integrated antenna with columnar feed line in accordance with embodiments described herein. As shown, three-dimensional substantially cage-shaped antenna 302, including feed line 328 and/or metal pad 404 can be cofire-integrated into CCM 301. The substantially cage-like configuration of antenna 402 is evident from the different views of antenna 402.

Figure 4D:
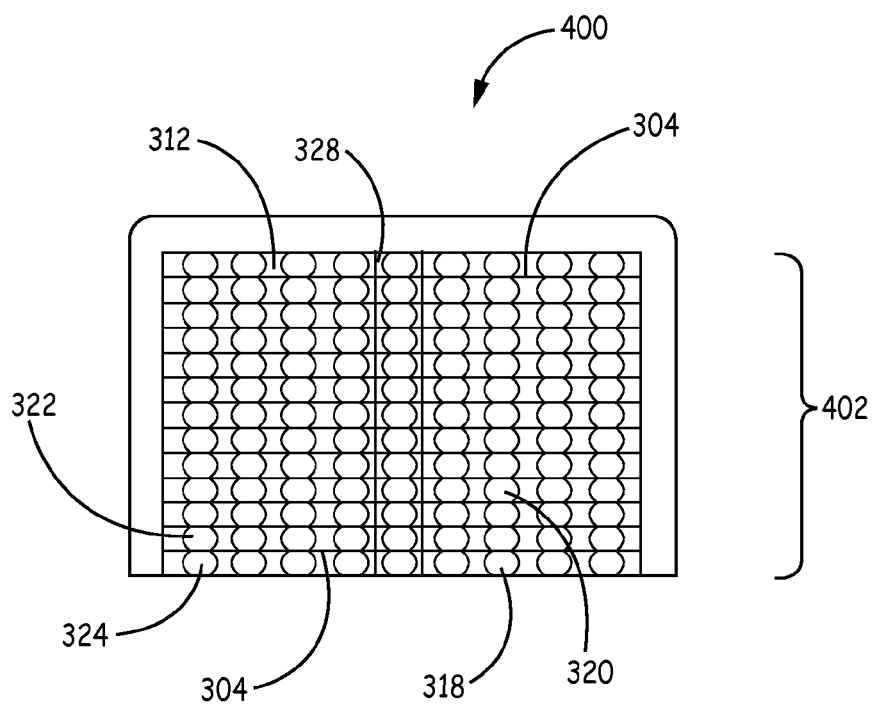
FIG. 4D illustrates a front view of an exemplary non-limiting CCM having a cofire-integrated antenna with columnar feed line in accordance with embodiments described herein.
Figure 4E:
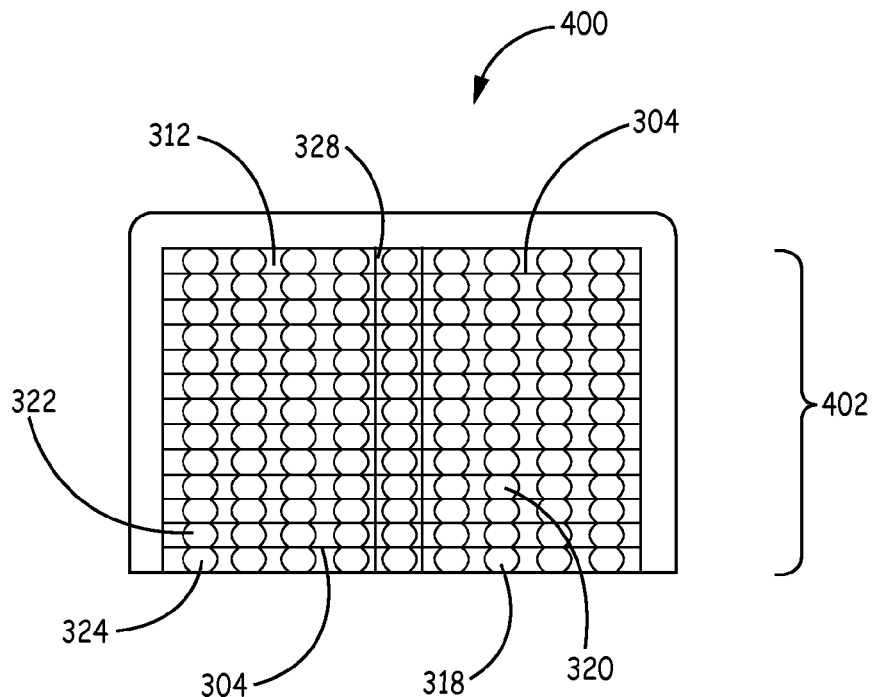
FIG. 4E illustrates a back view of an exemplary non-limiting CCM having a cofire-integrated antenna with columnar feed line in accordance with embodiments described herein.

FIG. 4D illustrates a front view of an exemplary non-limiting CCM having a cofire-integrated antenna with columnar feed line in accordance with embodiments described+herein. FIG. 4E illustrates a back view of an exemplary non-limiting CCM having a cofire-integrated antenna with columnar feed line in accordance with embodiments described herein. As shown, antenna 402 is positioned within CCM 400 and is formed in a substantially cage-like configuration.

Figure 4F:
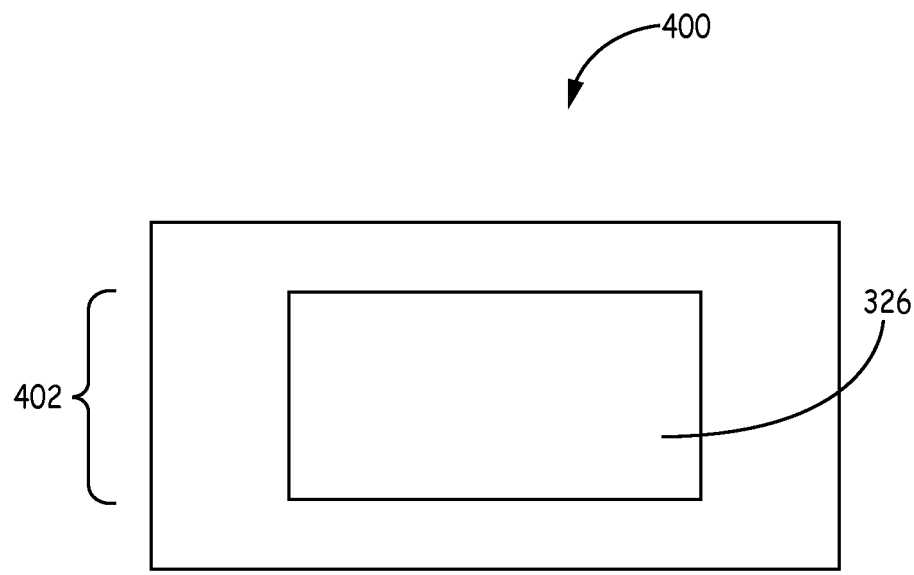
FIG. 4F illustrates a top view of an exemplary non-limiting CCM having a cofire-integrated antenna with columnar feed line in accordance with embodiments described herein.

FIG. 4F illustrates a top view of an exemplary non-limiting CCM having a cofire-integrated antenna with columnar feed line in accordance with embodiments described herein. Conductive plate 326 of antenna 402 is shown within CCM 400. In the embodiment shown, feed line 328 is provided on a single side of conductive plate 326 and does not protrude through conductive plate 326.

Figure 4G:
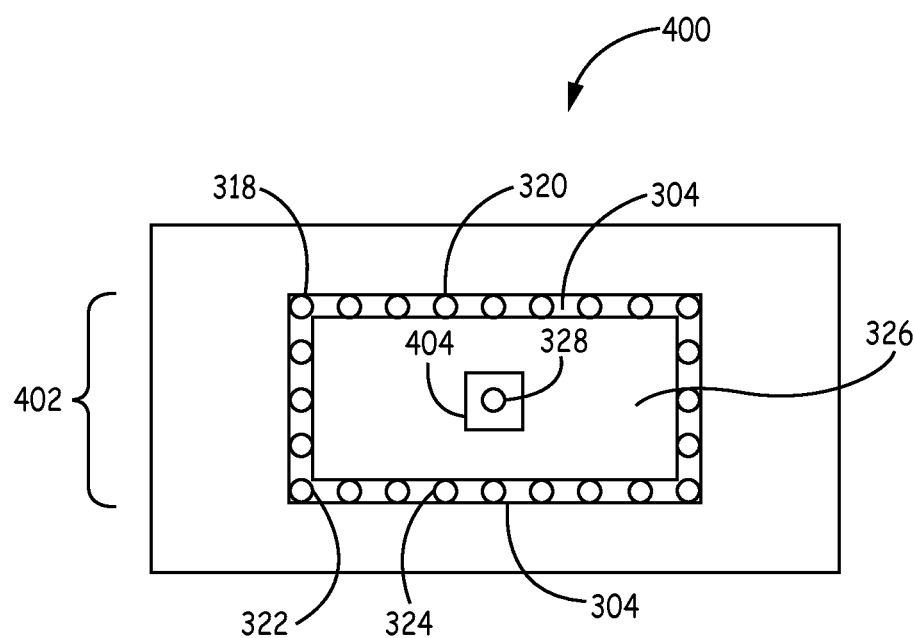
FIG. 4G illustrates a bottom view of an exemplary non-limiting CCM having a cofire-integrated antenna with columnar feed line in accordance with embodiments described herein.

FIG. 4G illustrates a bottom view of an exemplary non-limiting CCM having a cofire-integrated antenna with columnar feed line in accordance with embodiments described herein. Interconnections 318, 320, 322, 324 are vias shown coupled to conductive antenna elements 304 to form antenna 402. Feed line 328 and metal pad 404 are shown in a center region of antenna 402 coupled to conductive plate 326. In various embodiments, feed line 328 can be coupled to conductive plate 326 at any number of locations. For example, feed line 328 can be coupled to conductive plate 326 at an off-center location. As described above, the bottom of CCM 400 can provide a point of entry for a feed line 328 (or a connection to feed line 328) or any number of other connections (e.g., metal pad 404) between antenna 302 and a component in a housing of an IMD to which CCM 400 is coupled.

Figure 5:
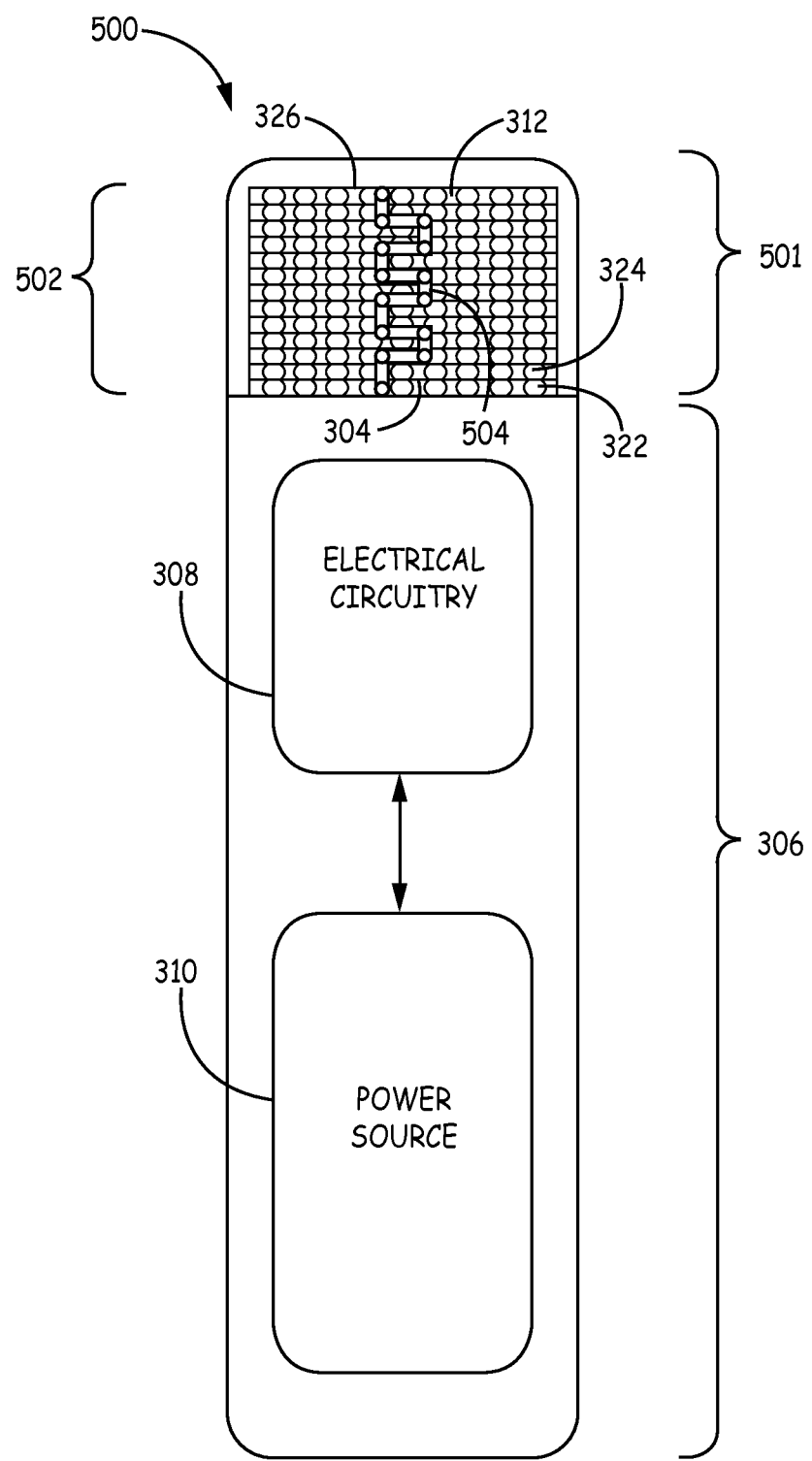
FIG. 5 illustrates a cross-sectional view of another exemplary non-limiting IMD having a CCM with cofire-integrated antenna and substantially serpentine-shaped feed line in accordance with embodiments described herein.

FIG. 5 illustrates a cross-sectional view of another exemplary non-limiting IMD having a CCM with cofire-integrated antenna and substantially serpentine-shaped feed line in accordance with embodiments described herein. In various embodiments, CCM 501 can include one or more of the structure and/or functionality of CCM 301, 400 (and vice versa). In various embodiments, antenna 502 can include one or more of the structure and/or functionality of antenna 302, 402 (and vice versa). Repetitive description of like elements employed in other embodiments is omitted for sake of brevity.

With reference to FIGS. 4A and 5, while feed line 328 is substantially columnar, feed line 504 is substantially serpentine-shaped. In some embodiments, feed line 504 can be formed from a plurality of via interconnections electrically coupled to one another. For example, three vertical vias can be alternately conductively coupled to intervening horizontal vias to generate the substantially serpentine-shaped feed line 504 shown in FIG. 5. By way of example, but not limitation, apertures can be provided in dielectric material 312 in the direction and layer corresponding to the direction (e.g., vertical y axis orientation or horizontal x-z axis orientation) and layer of feed line 504 at the particular layer of dielectric material 312. Conductive material from which interconnections are formed can be provided in the apertures to form feed line 504 upon co-firing.

Feed line 504 can be provided in a substantially serpentine shape to adjust the impedance of feed line 504 and/or antenna 302. Accordingly, use of feed line 504 can result in reduced impedance relative to use of feed line 328 of FIGS. 3 and 4A-4G. Further, in various embodiments, the length and/or configuration of feed line 504 can vary to further adjust the impedance. For example, in some embodiments, in lieu of providing three vertical portions in feed line 504, two, four or more vertical portions can be provided with intervening horizontal portions.

Figure 6A:
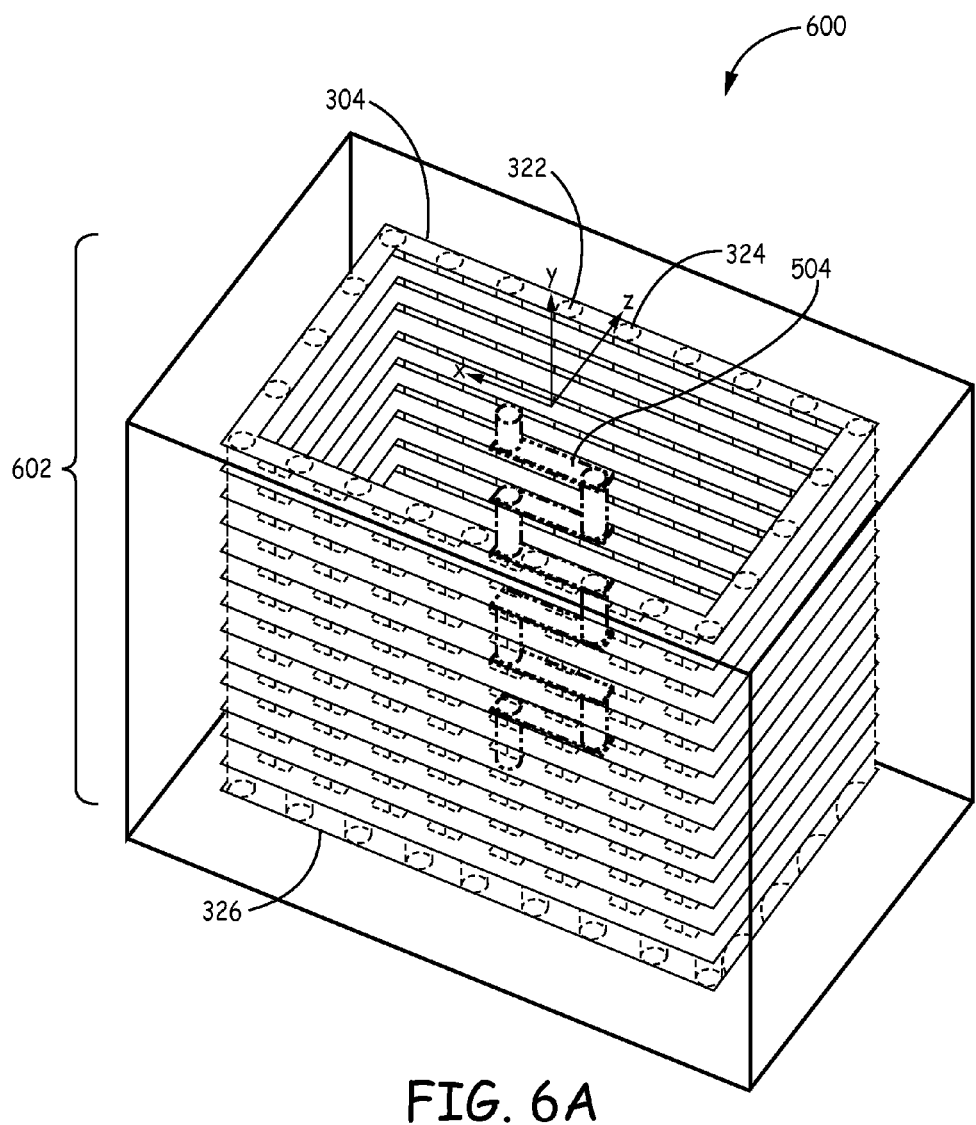
FIG. 6A illustrates a perspective view of an exemplary non-limiting CCM having a cofire-integrated antenna and substantially serpentine-shaped feed line in accordance with embodiments described herein.

FIG. 6A illustrates a perspective view of an exemplary non-limiting CCM having a cofire-integrated antenna and substantially serpentine-shaped feed line in accordance with embodiments described herein. As shown in FIG. 6A, antenna 602 is cofire-integrated into CCM 600, and includes conductive plate 326, conductive antenna elements 304, interconnections (e.g., interconnections 318, 320, 322, 324) and feed line 504. Repetitive description of like elements employed in other embodiments is omitted for sake of brevity.

In the embodiment shown in FIG. 6A, relative to the embodiment of antenna 402 in FIG. 4A, FIG. 6A shows a perspective view of the bottom of antenna 602. As described with reference to FIG. 4A, the first side of antenna 602 includes a planar conductive plate 326 while the second side of antenna 602 (which is opposite the first side of antenna 602) is open and provides the feed line (in this embodiment, feed line 504 while, in the embodiment shown in FIG. 4A, feed line 328 is provided). As such, feed line 504 can be conductively coupled to one or more elements outside of CCM 600. In some embodiments, although not shown, in one or more embodiments of FIGS. 6A-6E, a metal pad (e.g., metal pad 404 of FIG. 4A) can be provided on an exterior surface of CCM 600 to provide conductivity between feed line 504 to one or more components outside of CCM 600.

Figure 6B:
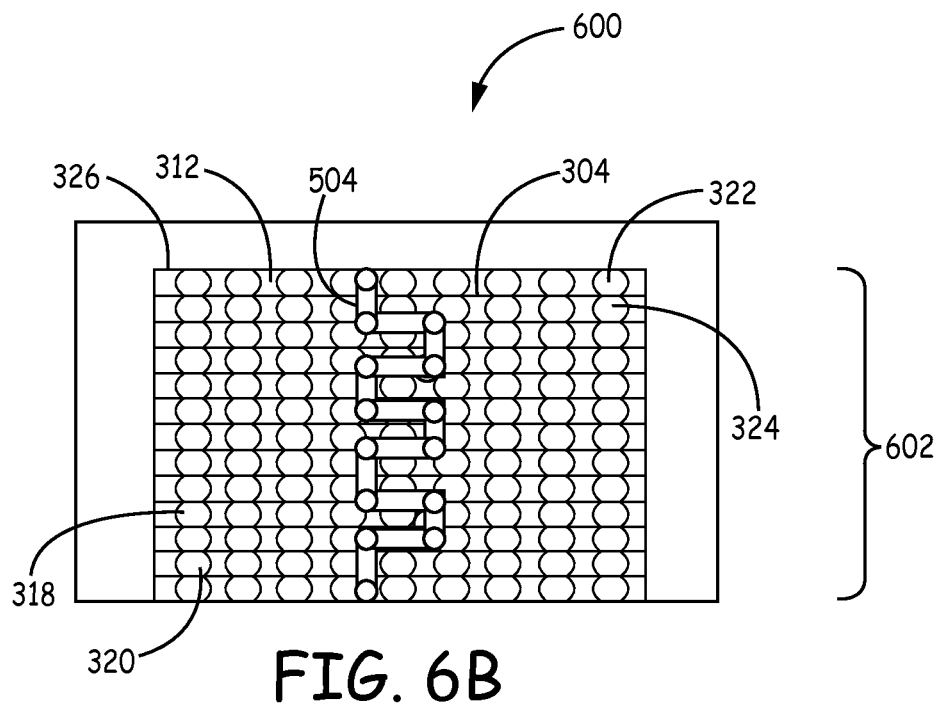
FIG. 6B illustrates a front view of an exemplary non-limiting CCM having a cofire-integrated antenna and substantially serpentine-shaped feed line in accordance with embodiments described herein.
Figure 6C:
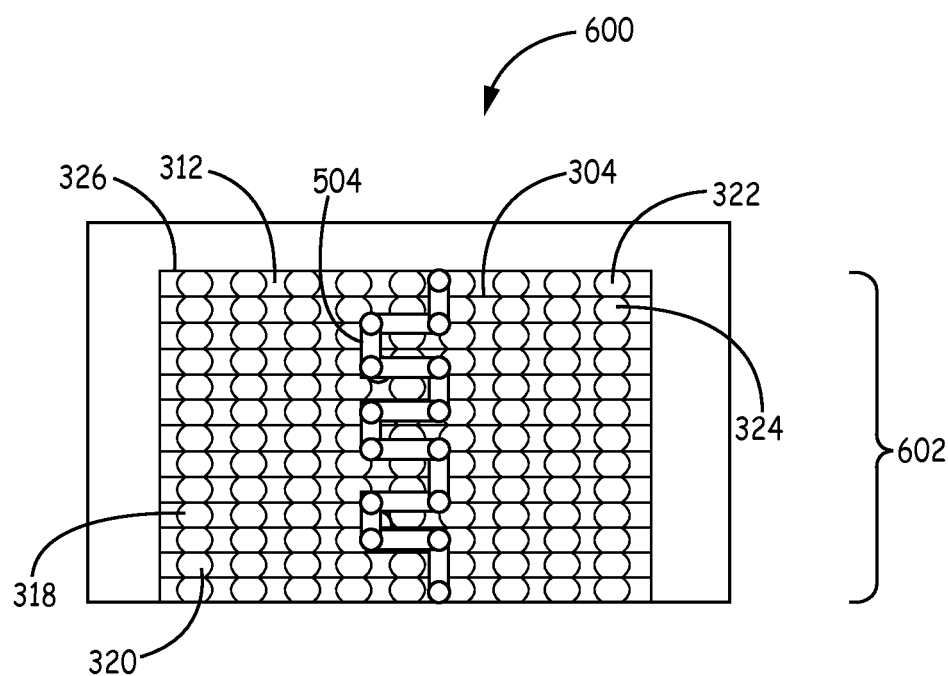
FIG. 6C illustrates a back view of an exemplary non-limiting CCM having a cofire-integrated antenna and substantially serpentine-shaped feed line in accordance with embodiments described herein.
Figure 6D:
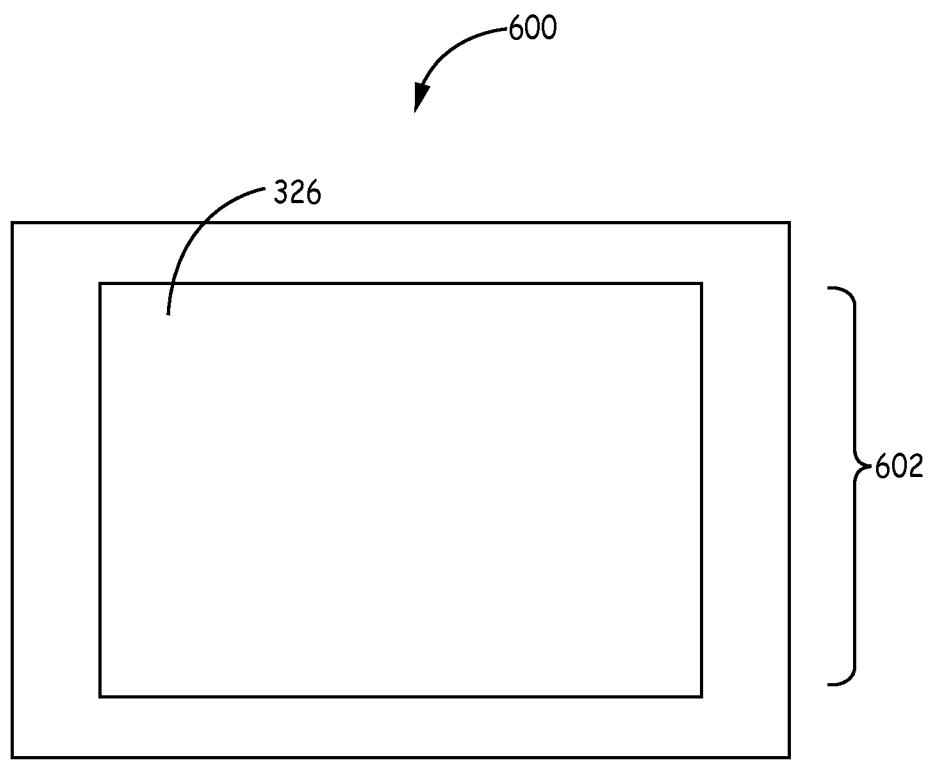
FIG. 6D illustrates a top view of an exemplary non-limiting CCM having a cofire-integrated antenna and substantially serpentine-shaped feed line in accordance with embodiments described herein.
Figure 6E:
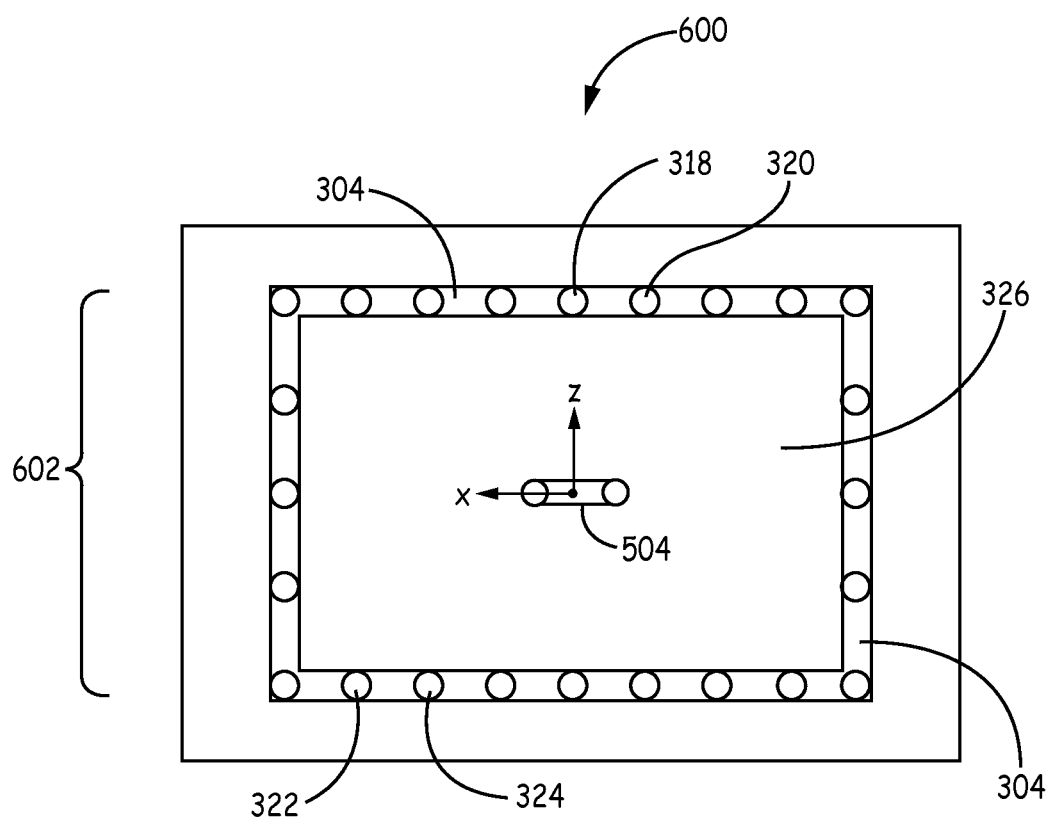
FIG. 6E illustrates a bottom view of an exemplary non-limiting CCM having a cofire-integrated antenna and substantially serpentine-shaped feed line in accordance with embodiments described herein.

FIG. 6B illustrates a front view of an exemplary non-limiting CCM having a cofire-integrated antenna and substantially serpentine-shaped feed line in accordance with embodiments described herein. FIG. 6C illustrates a back view of an exemplary non-limiting CCM having a cofire-integrated antenna and substantially serpentine-shaped feed line in accordance with embodiments described herein. FIG. 6D illustrates a top view of an exemplary non-limiting CCM having a cofire-integrated antenna and substantially serpentine-shaped feed line in accordance with embodiments described herein. FIG. 6E illustrates a bottom view of an exemplary non-limiting CCM having a cofire-integrated antenna and substantially serpentine-shaped feed line in accordance with embodiments described herein.

Figure 7:
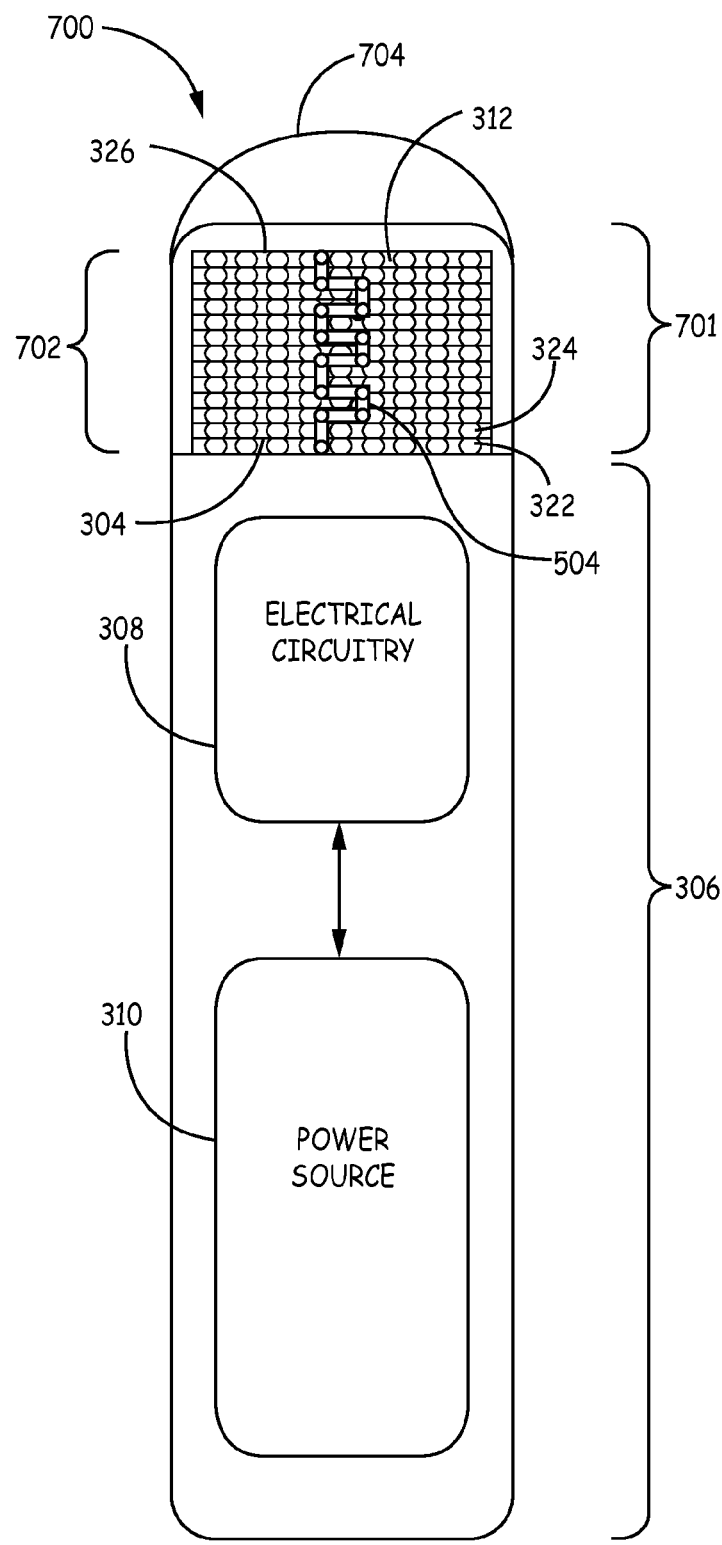
FIG. 7 illustrates a cross-sectional view of an exemplary non-limiting IMD having a CCM with cofire-integrated antenna, substantially serpentine-shaped feed line and cap in accordance with embodiments described herein.

FIG. 7 illustrates a cross-sectional view of an exemplary non-limiting IMD having a CCM with cofire-integrated antenna, substantially serpentine-shaped feed line and cap 704 in accordance with embodiments described herein. In various embodiments, IMD 700 can include one or more of the structure and/or functionality of IMD 102, 200, 300, 500 (and vice versa). Repetitive description of like elements employed in other embodiments is omitted for sake of brevity.

IMD 700 can include a CCM (e.g., CCM 701) having cofire-integrated three-dimensional substantially cage-shaped antenna 702 embedded in CCM 701. Further, while the embodiment shown at FIG. 7 includes feed line 504, in various embodiments, feed line 328 can be employed.

In some embodiments, although not shown, in one or more embodiments of FIG. 7, a metal pad (e.g., metal pad 404 of FIG. 4A) can be provided on an exterior surface of CCM 701 to provide conductivity between feed line 504 to one or more components outside of CCM 701.

CCM 701 can be adjoined to housing 306, and cap 704 can be adjoined to, or encapsulate, CCM 701 in various embodiments. For example, in some embodiments, to avoid or limit exposure to bodily fluids and/or gases, cap 704 can be placed over one or more portions of CCM 701.

Cap 704 can be adjoined to or integrally formed with CCM 701. For example, in some embodiments, cap 704 can be cofire-integrated with materials forming CCM 701 to fabricate a single structure. In other embodiments, cap 704 can be sealed to CCM 701 employing a hermetic sealing method. For example, cap 704 can be hermetically sealed to CCM 701 by metal brazing, glass joining or diffusion bonding approaches.

IMD 700 can also include electrical circuitry 308 and power source 310 configured to power IMD 700 (or one or more components of IMD 700). In various embodiments, one or more of CCM 602 having cofire-integrated antenna 702 embedded in CCM 701, housing 306, electrical circuitry 308 and/or power source 310 can be communicatively and/or electrically coupled to one another to perform one or more functions of IMD 700.

Figure 8:
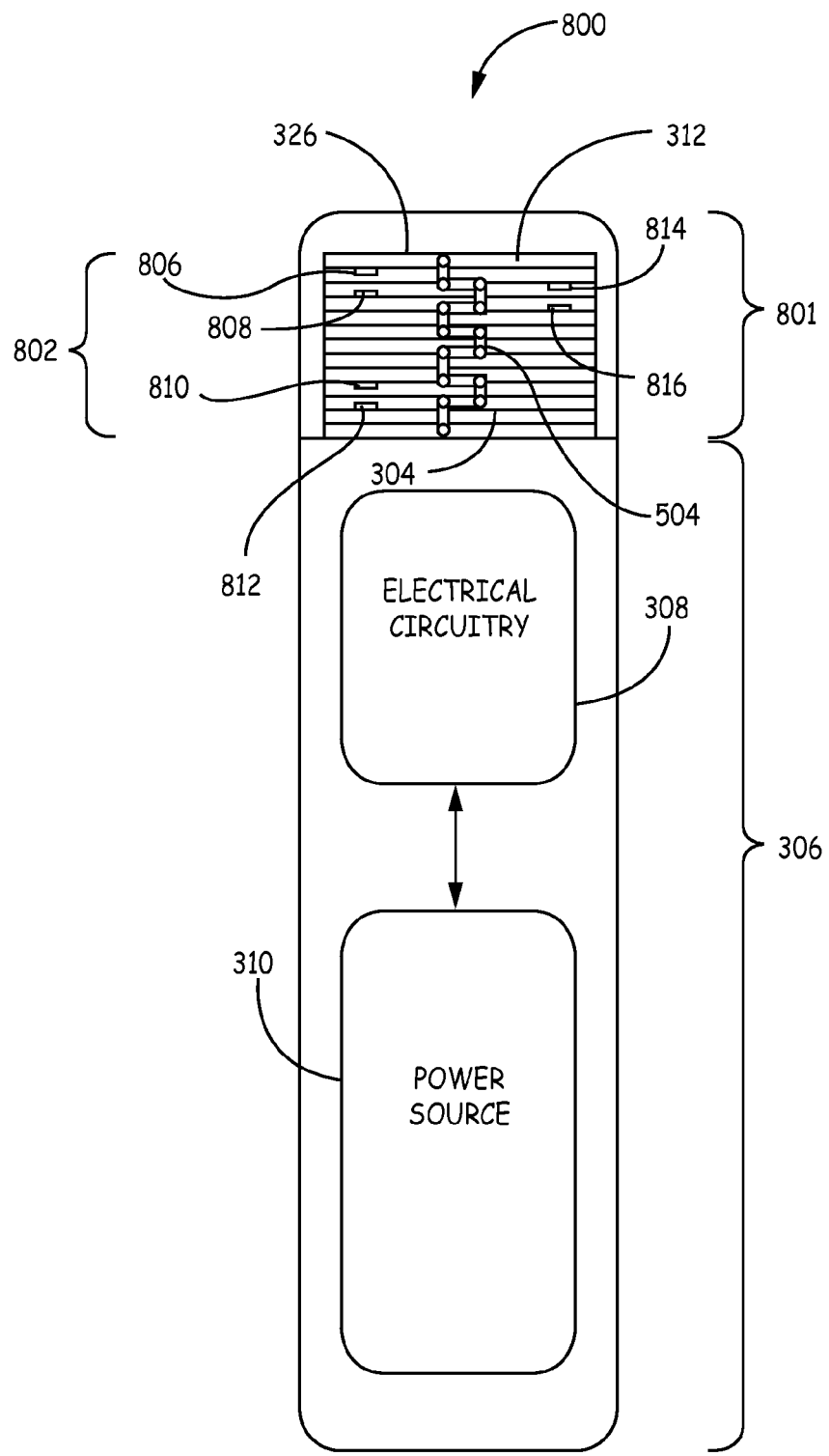
FIG. 8 illustrates a cross-sectional view of an exemplary non-limiting IMD having a CCM with cofire-integrated antenna with capacitive interconnections and substantially serpentine-shaped feed line in accordance with embodiments described herein.

FIG. 8 illustrates a cross-sectional view of an exemplary non-limiting IMD having a CCM with cofire-integrated antenna with capacitive interconnections and substantially serpentine-shaped feed line in accordance with embodiments described herein. In various embodiments, IMD 800 can include one or more of the structure and/or functionality of IMD 102, 200, 300, 500, 700, 800 (and vice versa). Repetitive description of like elements employed in other embodiments is omitted for sake of brevity.

IMD 800 can include a CCM (e.g., CCM 801) having cofire-integrated three-dimensional substantially cage-shaped antenna 802 embedded in CCM 801. In the embodiment shown in FIG. 8, in lieu of interconnections formed as vias (as shown and/or described with reference to FIGS. 3, 4A-4G, 5, 6A-6E and 7), interconnections 806, 808, 810, 812, 814, 816 can be capacitive interconnections post-cofiring to provide conductivity across one or more regions of CCM 801 and antenna 802. Further, while the embodiment shown at FIG. 8 includes a feed line 504, in various embodiments, feed line 328 can be employed. Antenna 802 will be described in greater detail with reference to FIGS. 9A-9E.

In some embodiments, although not shown, in one or more embodiments of FIG. 8, a metal pad (e.g., metal pad 404 of FIG. 4A) can be provided on an exterior surface of CCM 801 to provide conductivity between feed line 504 to one or more components outside of CCM 801. CCM 801 can be adjoined to housing 306 in various embodiments. As described above with reference to FIGS. 3 and/or 5, any number of different types of seals or adjoining methods can be employed.

Figure 9A:
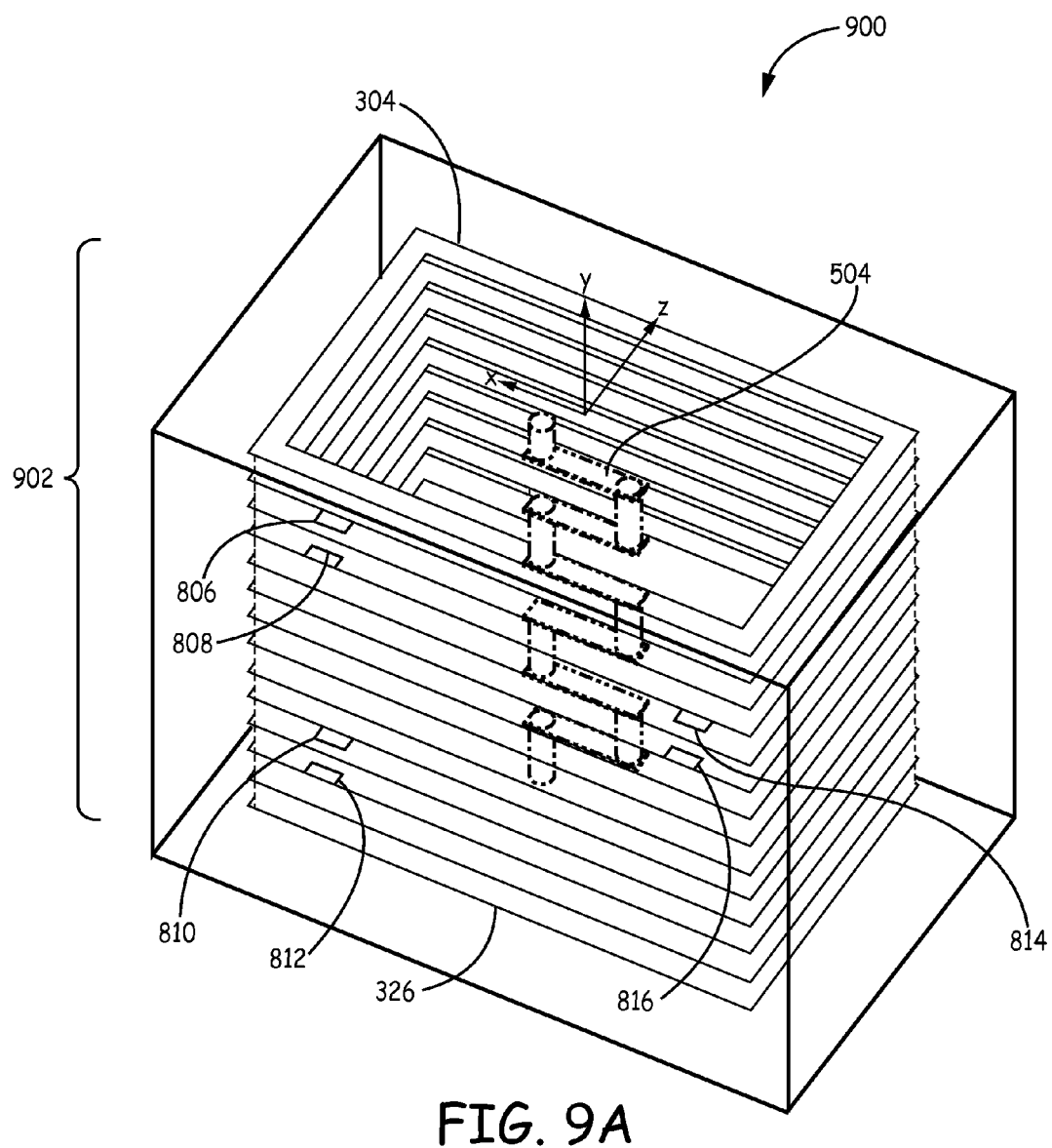
FIG. 9A illustrates a perspective view of an exemplary non-limiting CCM having a cofire-integrated antenna with capacitive interconnections and substantially serpentine-shaped feed line in accordance with embodiments described herein.

FIG. 9A illustrates a perspective view of an exemplary non-limiting CCM having a cofire-integrated antenna with capacitive interconnections and substantially serpentine-shaped feed line in accordance with embodiments described herein. Repetitive description of like elements employed in other embodiments is omitted for sake of brevity.

Shown is CCM 900 having three-dimensional substantially cage-shaped antenna 902 and capacitive interconnections provided on one or more layers of conductive antenna elements 304. In lieu of providing apertures for via interconnections (e.g., interconnections 318, 320, 322, 324 of FIG. 4A, for example) in layers of dielectric material 312 that, when cofired, form antenna 402, apertures can be provided between layers of conductive antenna elements 304 to provide conductive material forming metal pads or plates 806, 808, 810, 812, 814, 816 (capacitive interconnections) post-cofiring. As shown, pairs of metal pads 806, 808, 810, 812, 814, 816 can be positioned substantially parallel to one another and separated from one another by dielectric material 312 thereby forming a capacitive structure. In this manner, electricity is capacitively coupled from the metal pad on one layer (e.g., pads 806, 814, 810) to the metal pad on the other layer (e.g., pads 808, 816, 812, respectively) to provide conductivity through various portions of CCM 900 and antenna 902.

In various embodiments, different numbers and/or sizes of capacitive interconnections can be formed across antenna 902 based on desired conductivity after cofiring. For ease of illustration, however, FIG. 9A illustrate only three capacitive interconnections, e.g., a first capacitive interconnection formed by metal pads 806, 808, a second capacitive interconnection formed by metal pads 810, 812 and a third capacitive interconnection formed by metal pads 814, 816.

However, capacitive interconnections can be formed at each portion of antenna 902 in which via interconnections were provided in antenna 402 of FIGS. 4A-4E, for example. In other embodiments, the portions of conductive antenna elements 304 (e.g., traces) on different layers may be connected using both vias and capacitive interconnections, e.g., some portions connected using via interconnections and other portions connected using metal pads or plates forming capacitive interconnections.

In some embodiments, after cofiring, metal pads forming a capacitive interconnection (e.g., metal pads 810, 812) can be conductively coupled to a metal pad (not shown) in or on an exterior surface of, CCM 900. With reference to FIG. 8, the metal pad in or on the exterior surface of CCM 900 can be electrically coupled to a component outside of CCM 900.

There are several advantages to employing cofire-integrated capacitive interconnections in lieu of vias including, but not limited to, simplified design and manufacturing process, and added electromagnetic filtering functionality. The embodiments incorporating capacitive coupling can reduce or eliminate the need for vias in adjacent layers so the overall design may be simpler and cheaper. Further, by adjusting the size of the surface metal pads the capacitance can be tailored to filter out, or reduce the amount of, unwanted parasitic electromagnetic signals relative to embodiments having through hole via interconnections. Additionally, these configurations can provide the antenna with better impedance matching.

In some embodiments, feed line 504 can be coupled to a metal pad (e.g., metal pad 404 of FIG. 4A) to conductively couple to a component outside of CCM 900. Further, while the embodiment shown at FIG. 9A includes a feed line 504, in various embodiments, feed line 328 can be employed.

Figure 9B:
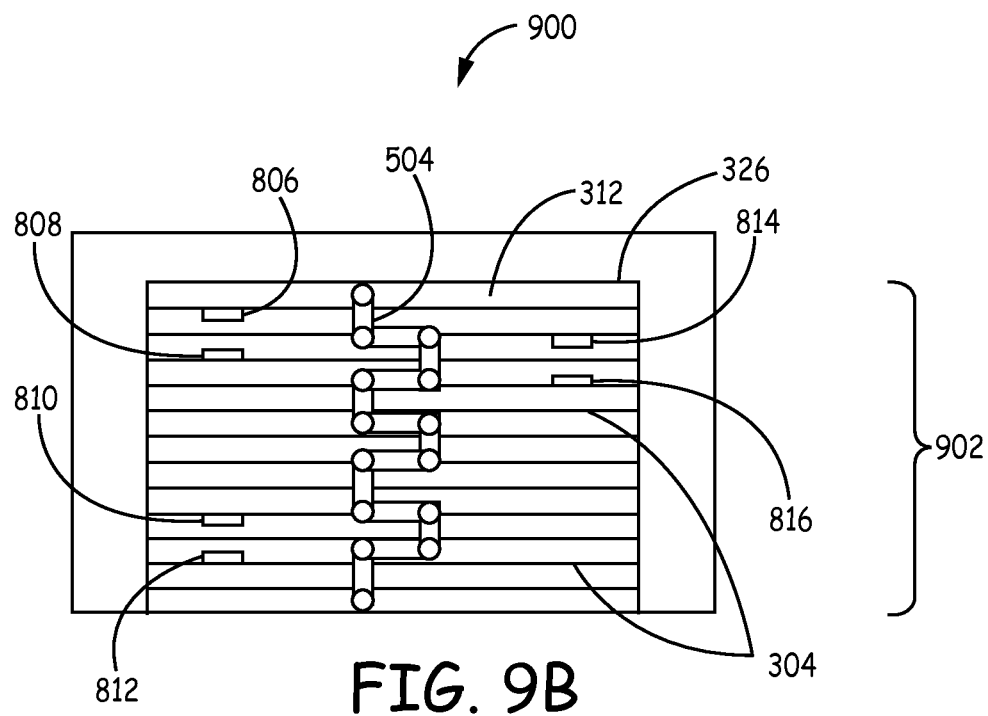
FIG. 9B illustrates a front view of an exemplary non-limiting CCM having a cofire-integrated antenna with capacitive interconnections and substantially serpentine-shaped feed line in accordance with embodiments described herein.
Figure 9C:
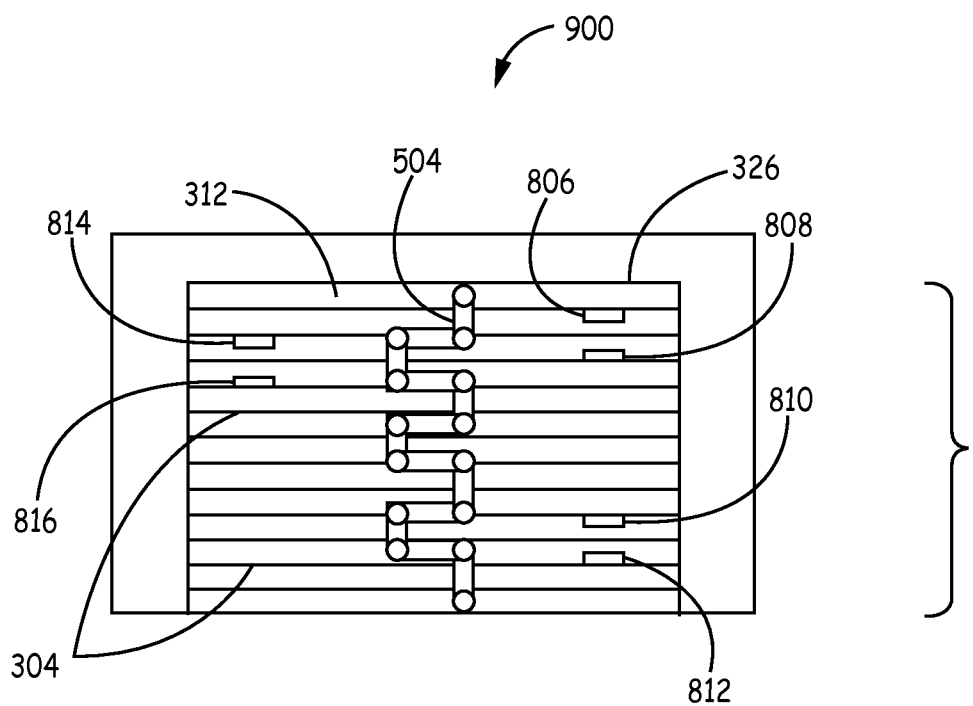
FIG. 9C illustrates a back view of an exemplary non-limiting CCM having a cofire-integrated antenna with capacitive interconnections and substantially serpentine-shaped feed line in accordance with embodiments described herein.
Figure 9D:
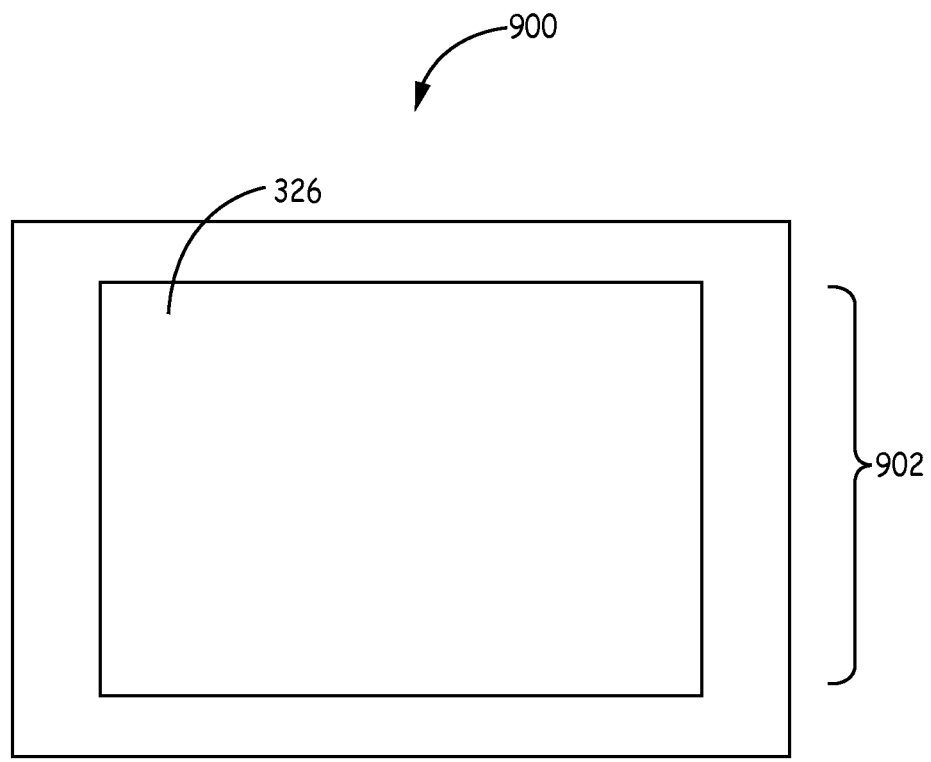
FIG. 9D illustrates a top view of an exemplary non-limiting CCM having a cofire-integrated antenna with capacitive interconnections and substantially serpentine-shaped feed line in accordance with embodiments described herein.
Figure 9E:
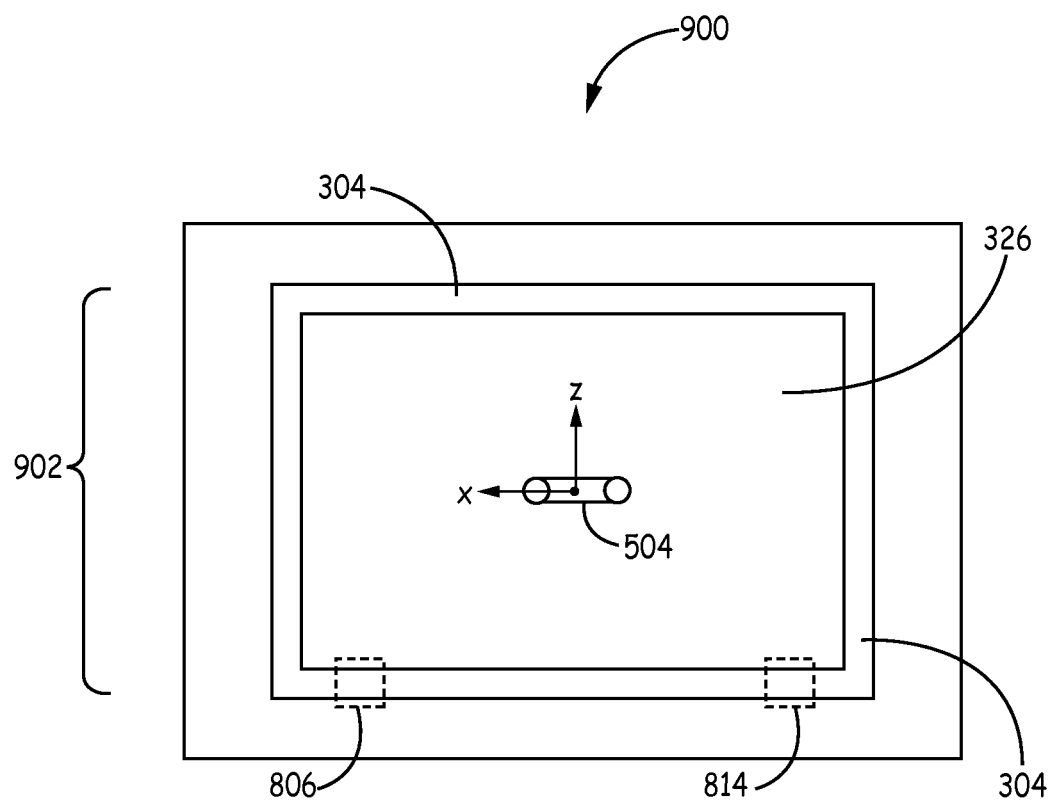
FIG. 9E illustrates a bottom view of an exemplary non-limiting CCM having a cofire-integrated antenna with capacitive interconnections and substantially serpentine-shaped feed line in accordance with embodiments described herein.

FIG. 9B illustrates a front view of an exemplary non-limiting CCM having a cofire-integrated antenna with capacitive interconnections and substantially serpentine-shaped feed line in accordance with embodiments described herein. FIG. 9C illustrates a back view of an exemplary non-limiting CCM having a cofire-integrated antenna with capacitive interconnections and substantially serpentine-shaped feed line in accordance with embodiments described herein. FIG. 9D illustrates a top view of an exemplary non-limiting CCM having a cofire-integrated antenna with capacitive interconnections and substantially serpentine-shaped feed line in accordance with embodiments described herein. FIG. 9E illustrates a bottom view of an exemplary non-limiting CCM having a cofire-integrated antenna with capacitive interconnections and substantially serpentine-shaped feed line in accordance with embodiments described herein.

In various embodiments, one or more of the CCMs described herein can be generated according to a cofire ceramic fabrication process that can advantageously facilitate size reduction of antennas and RF transparent structures employed in IMDs thereby increasing the potential for widespread medical device telemetry systems.

A non-limiting exemplary process for generating one or more of the CCMs described herein can include one or more of the following steps. One or more layers of dielectric material are independently processed, and the layers are subsequently collated and laminated to one another. The laminated structure can then be cut/diced into smaller portions corresponding to individual components/structures (when numerous components/structures are processed on a single dielectric layer). The cut/diced portions (or the entirety of the laminated structure in some embodiments) are cofired. The temperature profile employed during cofiring depends on a number of factors including, but not limited to, whether low temperature cofire ceramic (LTCC) materials or high temperature cofire ceramic (HTCC) materials are employed in the cofire structure.

In one embodiment, the dielectric material can be a tape generated by a tape casting process. Tape casting is a process employed to produce thin tapes (e.g., ceramic tapes) from ceramic slurry. One example process includes placing ceramic slurry in a chamber having a small gap controlled by a doctor blade. A polymer tape is then passed under the gap and slurry forms on the surface at the thickness dictated by the doctor blade gap. The slurry and tape pass through the oven, evaporating the liquid and forming a solid ceramic tape on a polymer backing. The tape then exits the oven and is wound onto a spool structure. While the above embodiment describes tape casting for generating the dielectric material, in other embodiments, the dielectric layer can be provided via a pre-formed ceramic green sheet such as produced by roll-compaction, extrusion or comparable processes.

In embodiments in which the CCM will be located inside of a hermetically sealed housing, the dielectric layer need not be composed of biocompatible and biostable ceramic material. However, in embodiments in which the CCM will not be located in a hermetically sealed housing (e.g., if the CCM will be located in a plastic header), the dielectric layer can be composed of biocompatible and biostable ceramic material. Exemplary biostable and/or biocompatible dielectric material can include, but is not limited to, oxides of aluminum, zirconium, silicon, niobium, tantalum, and mixtures of their oxides.

In other embodiments, dielectric layers that will be external surfaces to the CCM can be coated with material that is biostable and biocompatible while other dielectric layers can be non-biostable and non-biocompatible. Coating can be performed by a number of different methods including, but not limited to, chemical vapor deposition, physical vapor deposition, electron-beam evaporation sputtering or plating.

Dielectric layers can be composed of LTCC or HTCC material. LTCC material generally has a sintering temperature of less than about 1000° Celsius. By way of example, but not limitation, LTCC material can be glass bonded ceramics of composition that suitably densifies in the 850°-1000° Celsius range. In some embodiments, LTCC material can have a sintering temperature of between about 850° and 900° Celsius. HTCC material generally has a sintering temperature greater than about 1000° Celsius (and typically approximately 1600° Celsius). In some embodiments, HTCC material can have a sintering temperature of between about 1100° and 2100° Celsius. By way of example, but not limitation, HTCC material can be alumina and/or aluminum nitride.

In embodiments employing tape casting, the tape is cut to dimensions/shape suitable for the desired cofire structure/component. The result is a dielectric layer that can be processed in preparation for cofiring. In various embodiments, numerous dielectric layers can be processed in parallel or in series according to the above-described steps. The numerous layers can then be cofired together, simultaneously.

In some embodiments, one or more apertures are provided in the dielectric layer. For example, the apertures can be apertures for interconnections between layers of dielectric material that will form the CCM. As described, the apertures for interconnections can be apertures for via interconnections and/or apertures for capacitive interconnections. Numerous approaches can be employed for providing the apertures in the dielectric layer including, but not limited to, mechanical punching, laser drilling or mechanical drilling.

In some embodiments, one or more layers of dielectric material can be provided as layers that will be external surfaces of the CCM (after collating, laminating and cofiring).

The apertures for the interconnections can be provided at positions corresponding to desired locations of interconnections that will provide electrical connection between the layers of dielectric material after cofiring is completed. As such, aperture position corresponds to expected locations of conductive material that will form the antenna after cofiring. Other arrangements of aperture position are possible in accordance with the desired antenna configuration such that the interconnections are positioned to conductively couple to conductive antenna elements (e.g., traces).

Next, locations for post-firing interconnections are created by filling apertures with conductive paste. In various embodiments, conductive paste can be deposited to create a conductive path between the different layers of conductive antenna elements and dielectric material after cofiring. Specifically, the interconnections can form electrical interconnections along a y-axis of a cofire stack of numerous dielectric layers. The vias can be filled with the conductive paste using vacuum assisted screen printing in some embodiments.

Material associated with a feed line can be deposited in the apertures of dielectric as well so as to form a feed line upon cofiring. In various embodiments, the feed line can have any number of configurations including, but not limited to, columnar, substantially serpentine-shaped (to mitigate impedance) or the like.

In embodiments in which the CCM will be located inside of a hermetically sealed housing, the conductive paste can be conductive non-biocompatible and non-biostable material. Exemplary materials that are not biostable and not biocompatible that can be employed include, but are not limited to, copper, molybdenum and tungsten.

However, in embodiments in which the CCM will not be located in a hermetically sealed housing (e.g., if, for example, CCM will be located in a plastic header), conductive paste can be or include one or more conductive materials that are biostable and biocompatible. Conductive materials that are biostable can include, but are not limited to, platinum, palladium, platinum, iridium, silver-palladium, platinum-iridium, and/or mixtures including such conductive materials.

The determination of which biostable conductor materials to use can be a function of whether an LTCC or HTCC system will be employed for cofiring. For example, for LTCC systems, metals with lower melting temperatures can be employed. For HTCC systems, metals with higher melting temperatures can be employed (e.g., platinum, iridium, palladium and their mixtures).

Hermeticity of interconnections can be very advantageous towards long-term implantation of the CCM. Hermeticity can be achieved upon cofiring conductive paste having particular characteristics. For example, conductive pastes that include platinum and alumina combinations can result in hermetic vias upon cofiring (when the conductive material of the antenna includes or is alumina). In some embodiments, this conductive paste is combination of platinum (e.g., platinum powder) and an alumina (e.g., aluminum oxide, corundum) additive. For example, in some embodiments, the conductive paste can include 30% alumina, about 8% alumina or about 5% alumina.

In some embodiments, the platinum powder can be composed of a first platinum powder that has a median particle size between about 3 um and about 10 μm (e.g., $d_{50}$ median particle size), a second platinum powder having a median particle size between about 5 μm and about 20 μm or a combination of the first and second platinum powders. Use of particles of different size for the materials of the conductive paste, including the additives, can change the thermal expansion response and/or sintering kinetics and properties (e.g., sintering shrinkage, shrinking profile) of the conductive paste.

As noted above, the incorporation of the alumina additive in the platinum powder can result in a cofire hermetic bond between the interconnection and the conductive antenna elements in embodiments in which the antenna is composed of alumina. In particular, the alumina in the platinum powder can facilitate bonding with the alumina from which the antenna is composed along the boundary between the interconnection and the antenna. Such bonding at the boundary can increase the likelihood of achieving a hermetic seal (relative to embodiments that utilize conductive paste that does not include alumina). As such, incorporating alumina into the conductive paste (when the conductive material from which the antenna is composed is or also includes alumina) can result in a hermetic seal between the interconnection and the conductive antenna elements (e.g., traces). As such, in some cases, body fluids can be prevented from passing through the interconnection and damaging components of CCM and/or allowing leakage of materials integrated in the CCM to the patient. Long-term implantation can then be facilitated.

Next, screen printing of various materials for the antenna and/or components to be cofire-integrated can be provided on one or more dielectric layers. For example, metal elements (e.g., traces) for the antenna can be provided overlapping at least some portion of the conductive paste with which the interconnections are filled to facilitate electrical conductivity across numerous layers of the CCM after cofiring.

For example, in some embodiments, conductive paste forming a configuration of a plate can be deposited on one layer of dielectric material to provide a conductive plate of the antenna after cofiring. Further, one or more layers of conductive paste can be formed on one or more other layers of dielectric to provide conductive antenna elements (e.g., traces) after cofiring. The one or more layers of conductive paste to provide conductive antenna elements can be formed in the configuration of annular substrates having perimeters substantially coextensive with the perimeter of the conductive paste that will form the plate.

As noted, screen printing can be employed in some embodiments to perform the metal deposition. Screen printing is a thick film technology that includes pushing ink through a patterned screen or stencil having cutout regions coinciding with a desired design and/or location of materials on a surface. The material printed on the layer can be cured at a modest temperature (e.g., 50° Celsius to 200° Celsius) to dry and fix the material temporarily in position on the layer. In some embodiments, the material can be cured by exposure to ultraviolet (UV) light.

The conductive material can be screen printed in a configuration suitable to the design of the eventual antenna, including interconnections and/or feed line. By way of example, but not limitation, the conductive antenna elements (e.g., metal traces) of the antenna can be formed in the dielectric material. For example, the conductive antenna elements can be printed on the same layers of dielectric material as layers on which interconnections are provided.

The conductive material can be provided in connection with the conductive paste to provide electrical conductivity between the antenna and the interconnections thereby facilitating conductivity across layers of the CCM. While screen printing is described, in other embodiments, different approaches for material deposition can be employed. Deposition approaches can include, but are not limited to, direct writing, plating, spraying or the like.

Portions of conductive material can be located at different positions on the layers of dielectric material based on the desired configuration of the antenna to be formed from the conductive material. By way of example, but not limitation, the conductive material can be placed in a first set of positions on a dielectric layer if a rectangular prismatic cage-like structure for the antenna is desired and/or placed in a second set of positions on a dielectric layer if a substantially cuboid structure for the antenna is desired.

In some embodiments, the two layers of dielectric material that will be closest to an external surface of the CCM after cofiring can be provided without conductive material. As such, there will be at least two layers of dielectric between metal and the surface of the CCM that will contact bodily tissue.

In embodiments in which the antenna will not be encased in a hermetically sealed housing, the conductive material can be biostable and/or biocompatible. Exemplary biostable and/or biocompatible dielectric material can include, but are not limited to those described supra for conductive paste of the interconnection.

In embodiments in which the antenna will be encased in a hermetically sealed housing, and therefore not likely to be exposed to bodily fluid and/or gases, the conductive material need not be biostable and biocompatible. Exemplary biostable and/or biocompatible dielectric material can include, but are not limited to those described supra for conductive paste of the interconnection.

While the above step describes screen printing of conductive material for the antenna, in various other embodiments, other components can be cofire integrated into a CCM and/or fabricated in or on or communicatively coupled to a CCM after cofire integration of a CCM and an antenna. The component can include any number of different types of components configured to perform an electrical function, including, but not limited to, a telemetry module (e.g., transmitter, receiver, transceiver or RF chip), one or more sensing electrodes, one or more passive elements (e.g., capacitors and/or inductors) or an entire impedance matching network for an antenna (e.g., antenna 302). The impedance matching network can modify the impedance of the antenna to desired levels, for example.

For example, material for some types of passive electrical components can be deposited onto one or more layers of dielectric material. As another example, material for a passive network can be deposited onto one or more dielectric layers. In some embodiments, due to the temperature at which cofiring of a CCM (e.g., CCM 301) occurs, both passive and active components can be included in the CCM after the cofiring process has been completed.

Upon cofiring, the antenna, including the feed line and interconnections, and, in some embodiments, a component, can be cofire-integrated, at least in part, into the CCM. As such, greater functionality can be integrated into the CCM as desired thereby reducing the footprint of the overall IMD.

The numerous layers of dielectric material are collated and laminated to form a laminated structure. Lamination is performed at modest heat with pressure applied to the stack of layers to cause the stack of layers to adhere to one another. Accordingly, geometric registration can be maintained between the dielectric layers (and vias). Lamination can also cause a slight densification of the material provided on the layers, which can result in more effective sintering during cofiring. In some embodiments, lamination includes applying 3000 pounds per square inch (psi) at 70-80° Celsius for approximately 10 minutes. In various embodiments, however, the temperature and time during which the collated stack is heated can vary.

Next, the laminated structure is cofired and the CCM results. For example, with reference to FIG. 3, the CCM can be CCM 301 while, with reference to FIG. 4A, the CCM can be CCM 400. Cofiring refers to the process of simultaneously sintering the ceramic and all materials deposited within/on the ceramic to densify the laminated structure. The temperature at which the laminated structure is cofired depends on the nature of the materials of which the dielectric layer is composed. For example, for LTCC materials, cofiring at between 850° Celsius and 900° Celsius can be employed. For HTCC materials, cofiring at about 1600° Celsius can be employed.

Although not shown, in embodiments in which numerous structures are being fabricated on each layer, prior to cofiring, the laminated structure can be cut/diced into numerous portions corresponding to the different locations of the structures being fabricated. For example, the laminated structure can be cut into four different portions corresponding to the locations of four CCMs being fabricated.

Conventional wafer dicing methods can be employed in some embodiments. Methods can include, but are not limited to, scribing and breaking, mechanical sawing or laser cutting.

The above description illustrates one example of a method of fabricating a CCM having a cofire-integrated antenna. Other embodiments can differ in any number of ways including, but not limited to, number of layers of dielectric material collated and laminated, the configuration of the conductive plate and/or conductive antenna elements, whether capacitive interconnections or via interconnections are employed, the type of materials employed, the locations or types of the interconnections, the configuration of the feed line, the components cofired in the CCM in addition to the antenna or the like. For example, as described with reference to FIGS. 8 and 9A-9E, in some embodiments, dielectric material for forming capacitive interconnections can be provided on the conductive material prior to cofiring to form capacitive interconnections between portions of the antenna to provide electrical connectivity (in lieu of forming vias between portions of the antenna).

Cofire ceramic technology can advantageously enable efficient antenna designs for IMDs because complex antenna designs can be facilitated and unique dielectric properties of the CCM resulting from the cofire process can better match body tissue inside the human body. Further, one or more embodiments described herein can facilitate significant RF performance, and thereby enable satisfactory RF signal ranges.

In the above-described embodiment, tape casting is performed as a first step. However, in other embodiments, in lieu of employing tape casting, a pre-formed ceramic green sheet, or green tape, can be employed.

Figure 10:
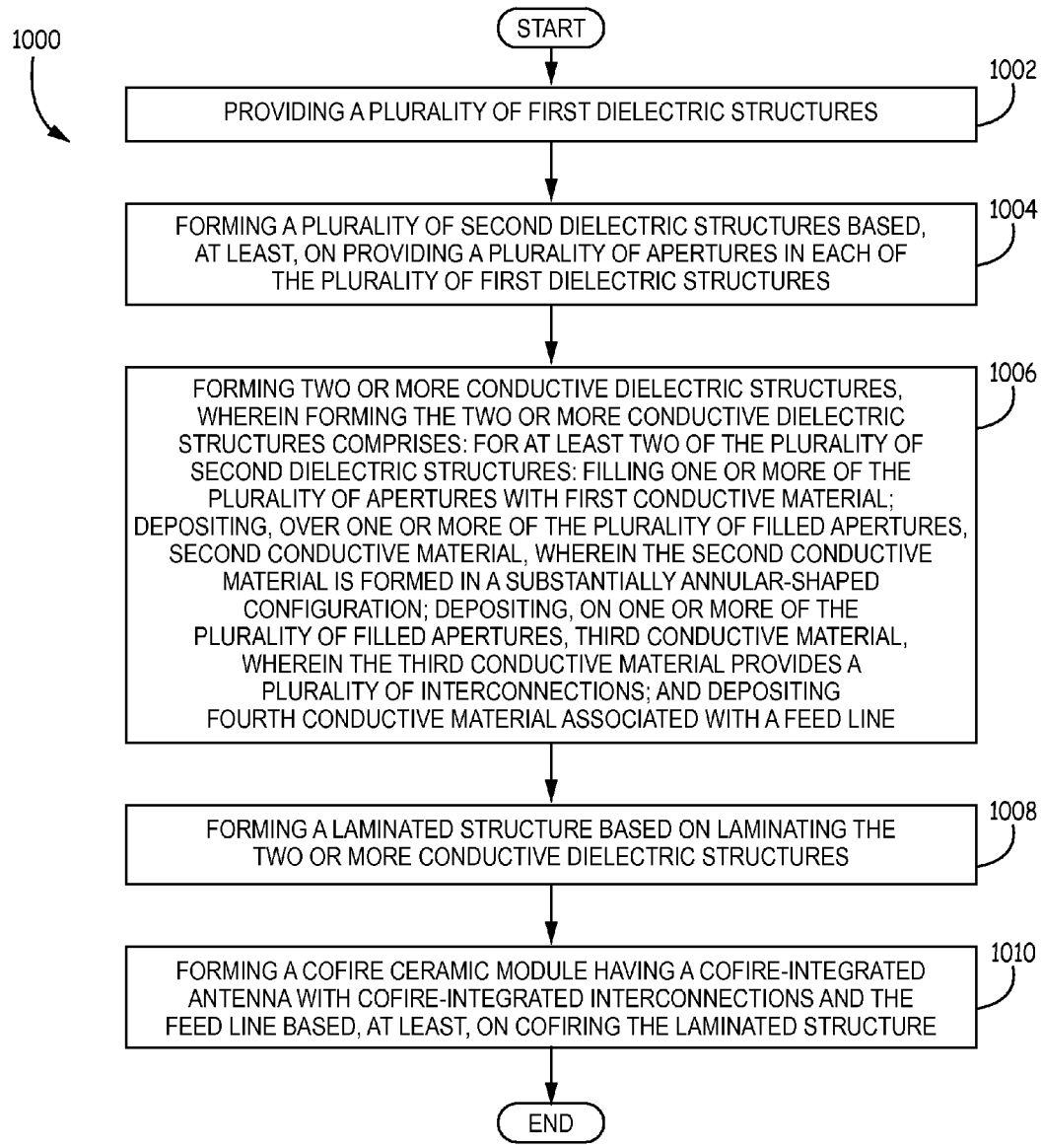
FIGS. 10 and 11 illustrate flow charts of exemplary non-limiting methods of fabricating IMDs in accordance with embodiments described herein.
Figure 11:
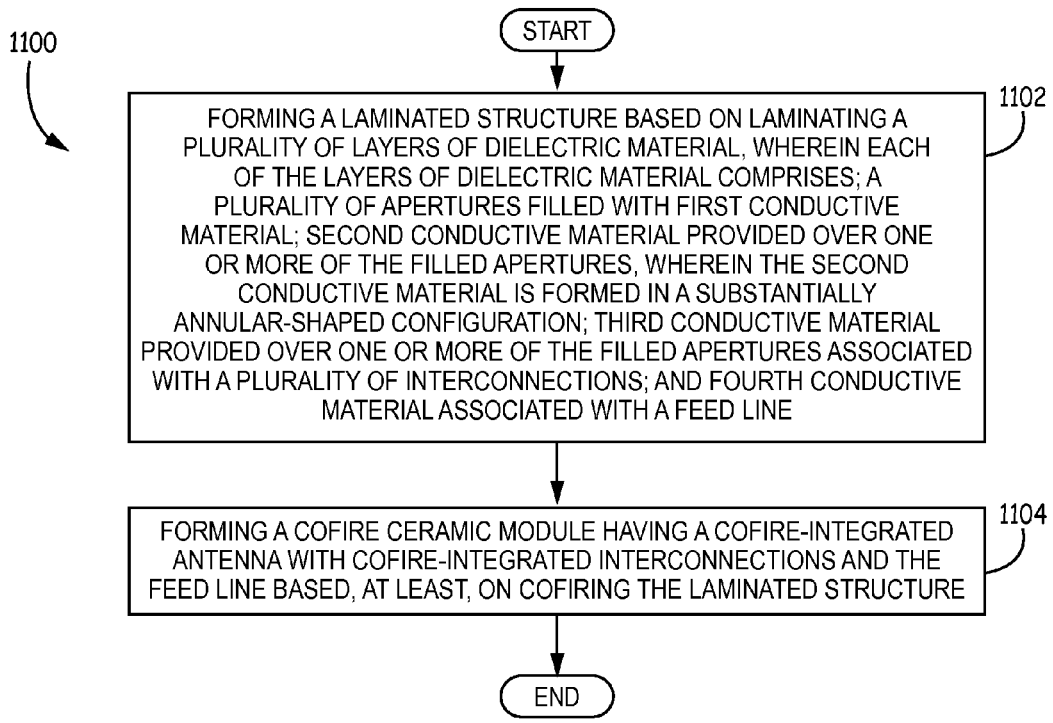

FIGS. 10 and 11 illustrate flow charts of exemplary non-limiting methods of fabricating IMDs in accordance with embodiments described herein. Turning first to FIG. 10, at 1002, method 1000 can include providing a plurality of first dielectric structures. For example, in some embodiments, the first dielectric structures can be tapes generated by a tape casting process. Two or more tapes can be employed for preparing structures that will be laminated and subsequently cofired, for example.

At 1004, method 1000 can include forming a plurality of second dielectric structures based, at least, on providing a plurality of apertures in each of the plurality of first dielectric structures provided at 1002. Apertures can be formed according to the desired location of conductive material forming the antenna, interconnections and/or any components to be cofire-integrated into the CCM post-cofiring.

At 1006, method 1000 can include forming two or more conductive dielectric structures. The two or more conductive dielectric structures can be formed from two or more of the second dielectric structures formed at 1004. Accordingly, two separate conductive dielectric structures can be formed and the structures can then be laminated to one another in 1008.

With regard to the conductive dielectric structures formed in 1006, in some embodiments, each of the conductive dielectric structures can be formed by the following process: filling one or more of the plurality of apertures with first conductive material; and depositing, over one or more of the plurality of filled apertures, second conductive material, wherein the second conductive material is formed in a substantially annular-shaped configuration. For example, one or more layers of the second conductive material can be material from which conductive antenna elements, or traces, of the antenna are to be formed post-cofiring.

The conductive dielectric structures can further be formed by depositing, on one or more of the plurality of filled apertures, third conductive material, wherein the third conductive material provides a plurality of interconnections; and depositing fourth conductive material associated with a feed line.

In various embodiments, one or more of the first, second, third and/or fourth conductive material can be the same material. For example, the second and third conductive material, which can be formed in a substantially annular-shaped configuration, and which can provide the plurality of interconnections, respectively, can be the same conductive material. In some embodiments, the interconnections can be interconnections 318, 320, 322, 324. In some embodiments, the interconnections can be shaped to form vias directly coupling layers of conductive antenna elements, for example.

In some embodiments, the fourth conductive material associated with the feed line can be conductive material used to form feed line 328 or feed line 504. As described, the feed line can be formed in a columnar configuration or a serpentine configuration. Other configurations are also possible based on the particular placement of the fourth conductive material that forms the feed line post-cofiring.

At 1008, method 1000 can include forming a laminated structure based on laminating at least the two or more conductive dielectric structures formed at 1006. For example, the two or more conductive dielectric structures can be vertically stacked and subsequently laminated.

Although not shown, in various embodiments, the laminated structure can also include a layer of dielectric material having a substantially continuous coat of conductive material on the surface of the dielectric material. For example, a tape can be substantially covered with conductive material. The two or more conductive dielectric structures formed at 1006, and the coated layer of dielectric material, can be vertically stacked with the coated layer of dielectric material provided on one end of the stack. The coated layer of dielectric material can form conductive plate 326, which provides a top layer of the antenna (e.g., antenna 302) formed post-cofiring.

In some embodiments, the substantially annular-shaped configuration of the second conductive material formed at 1006 can have a perimeter substantially co-extensive with the perimeter of the conductive material that coats the dielectric material to form conductive plate 326.

At 1010, method 1000 can include forming a CCM having a cofire-integrated antenna with cofire-integrated interconnections and the feed line based, at least, on cofiring the laminated structure. In some embodiments, the CCM formed after cofiring can be CCM 301, 400, 501, 600 and/or 701, for example.

In the embodiment described with reference to 1006, the conductive dielectric structures that include the second conductive material is formed in a substantially annular-shaped configuration on the dielectric layers, and the feed line material is provided through the dielectric layers. In some embodiments, in lieu of employing the dielectric tape in the interior region inside of the substantially annular-shaped configuration, a cavity can be provided through each of the dielectric layers in a region interior to the region covered by the substantially annular-shaped configuration. As such, air within an interior cavity can be provided as a dielectric in some embodiments.

In some embodiments, although not shown, method 1000 can also include adjoining the CCM to a housing. In some embodiments, adjoining the CCM to the housing is performed via generating a hermetic seal between the CCM and the housing. Further, in some embodiments, although not shown, method 1000 can also include electrically coupling a component of the housing to the feed line.

Turning now to FIG. 11, at 1102, method 1100 can include forming a laminated structure based on laminating a plurality of layers of dielectric material. In various embodiments, one or more (or all) of the layers of dielectric material include a plurality of apertures filled with first conductive material; and second conductive material provided over one or more of the filled apertures, wherein the second conductive material is formed in a substantially annular-shaped configuration. The layers of dielectric material can also include: third conductive material provided over one or more of the filled apertures associated with a plurality of interconnections; and fourth conductive material associated with a feed line.

Although not shown, in various embodiments, the laminated structure can also include a layer of dielectric material having a substantially continuous coat of conductive material on the surface of the dielectric material. For example, a tape can be substantially covered with conductive material. The coated layer of dielectric material can be vertically stacked with the layers of dielectric material described in 1102. For example, the coated layer can be provided on one end of the vertical stack. The coated layer of dielectric material can form conductive plate 326, which provides a top layer of the antenna (e.g., antenna 302) formed post-cofiring.

At 1104, method 1100 can include forming a CCM having a cofire-integrated antenna with cofire-integrated interconnections and the feed line based, at least, on cofiring the laminated structure. In some embodiments, the CCM can be CCM 301, 400, 501, 600 and/or 701.

In some embodiments, although not shown, method 1100 can also include adjoining the CCM to a housing. In some embodiments, adjoining the CCM to the housing is performed via generating a hermetic seal between the CCM and the housing. Further, in some embodiments, although not shown, method 1100 can also include electrically coupling a component of the housing to the feed line.

In some embodiments, a CCM can include an antenna incorporated with one or more components. Examples of components include, but are not limited to, a feedthrough, a telemetry module (e.g., transmitter, receiver, transceiver or RF chip), a sensing electrode, a passive element (e.g., capacitor or inductor) or an entire impedance matching network for the antenna.

The antenna can include the structure and/or functionality of any number of the different embodiments of antennas described herein. Example structures of feedthroughs that can be incorporated with the antenna in the CCM are as shown and/or described in U.S. Pat. No. 8,588,916, titled "Feedthrough configured for interconnect" and issued Nov. 19, 2013, the entirety of which is incorporated herein by reference.

Some of the embodiments, such as those described with reference to medical telemetry system 100 of FIG. 1 or medical telemetry system 100' of FIG. 2 can be practiced in computing environments. In these environments, certain tasks can be performed by remote processing devices that are linked through a communications network. Also, some of the embodiments include computing devices (e.g., external device 104) having computer-executable instructions that can be executed by processors to perform one or more different functions. Those skilled in the art will recognize that the embodiments can be also implemented in combination with hardware and/or software.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices (e.g., via access requests, queries or other data retrieval protocols) for a variety of operations with respect to the information stored by the medium.

In this regard, the term "tangible" herein as applied to storage, memory or computer-readable media, is to be understood to exclude only propagating intangible signals per se as a modifier and does not relinquish coverage of all standard storage, memory or computer-readable media that are not only propagating intangible signals per se. In this regard, the term "non-transitory" herein as applied to storage, memory or computer-readable media, is to be understood to exclude only propagating transitory signals per se as a modifier and does not relinquish coverage of all standard storage, memory or computer-readable media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable medical device (IMD), comprising:
a housing configured for one of human implant or being worn on a body; and
a cofire ceramic module coupled to the housing, wherein the cofire ceramic module includes an antenna cofire-integrated in the cofire ceramic module, the antenna comprising:
a plate composed of conductive material;
a plurality of layers of conductive antenna elements, the plurality of layers of conductive antenna elements being annular substrates having perimeters substantially coextensive with a perimeter of the plate;
a plurality of interconnections, wherein the plurality of interconnections comprise:
a first set of interconnections coupled between the plate and the conductive antenna element of one of the plurality of layers of conductive antenna elements; and
a second set of interconnections coupled between the conductive antenna elements of the remainder of the plurality of layers of conductive antenna elements; and
a feed line conductively coupled to the plate.

2. The IMD of claim 1, wherein the plurality of interconnections extend along a first axis and the plurality of layers of conductive antenna elements lie in planes that are substantially perpendicular to the first axis such that the antenna forms a substantially cage-shaped configuration.

3. The IMD of claim 1, wherein the annular substrates are at least one of substantially square annular substrates or substantially rectangular annular substrates.

4. The IMD of claim 1, further comprising:
a component configured to perform an electrical function or provide electrical conductivity with the cofire ceramic module.

5. The IMD of claim 4, further comprising a communication module disposed in the housing.

6. The IMD of claim 5, wherein the component comprises a metal pad cofire-integrated in the cofire ceramic module, and wherein the metal pad is configured to provide conductivity between the antenna and the communication module.

7. The IMD of claim 4, wherein the component comprises at least one of an active electrical component or a passive electrical component, and wherein the component is disposed in the housing.

8. The IMD of claim 4, wherein the component is at least one of a sensing electrode, a capacitor, an inductor or a matching circuit for the antenna.

9. The IMD of claim 1, wherein the plurality of interconnections comprises a plurality of substantially capacitive interconnections.

10. The IMD of claim 1, wherein the plurality of interconnections comprises a plurality of via interconnections.

11. The IMD of claim 1, wherein the feed line is substantially serpentine-shaped.

12. The IMD of claim 1, wherein the cofire ceramic module comprises a low temperature cofire ceramic material having a sintering temperature less than about 1000° Celsius.

13. The IMD of claim 1, wherein the cofire ceramic module comprises a high temperature cofire ceramic material having a sintering temperature greater than about 1000° Celsius.

14. The IMD of claim 1, wherein the cofire ceramic module comprises material or mixtures composed of at least one of zirconium, silicon, niobium, tantalum or an oxide of aluminum.

15. The IMD of claim 1, wherein the plurality of conductive antenna elements comprises material or mixtures composed of at least one of platinum, palladium, iridium, silver-palladium or platinum-iridium, niobium or tantalum.

16. The IMD of claim 1, wherein the plurality of conductive antenna elements comprises material or mixtures composed of at least one of molybdenum or tungsten.

17. The IMD of claim 1, wherein the housing is coupled to a first end of the cofire ceramic module.

18. The IMD of claim 1, wherein the housing comprises a polymeric material.

19. The IMD of claim 1, further comprising:
a power source within the housing; and
electrical circuitry within the housing.

20. The IMD of claim 1, wherein the IMD comprises at least one of an implantable therapy lead, an implantable sensor, an implantable monitor, an implantable cardioverter defibrillator, an implantable neurostimulator, an implantable physiological monitor or an implantable pulse generator.

21. The IMD of claim 1, wherein the antenna is configured to communicate information indicative of at least one of a command associated with functionality of the IMD, a parameter associated with a setting for the IMD or a remaining battery life of the IMD.

22. The IMD of claim 1, wherein the antenna is configured to communicate information indicative of at least one of a biological event of a wearer of the IMD or data generated by the IMD.

23. The IMD of claim 1, wherein the antenna is a first antenna and is configured to perform at least one of intrabody communication with a second antenna in a body of a wearer of the IMD or interbody communication with a second antenna outside of the body of the wearer of the IMD.

* * * * *